United States Patent [19]

Takeuchi et al.

[11] Patent Number: 4,797,362

[45] Date of Patent: Jan. 10, 1989

[54] ALKALINE PROTEASES AND MICROORGANISMS PRODUCING SAME

[75] Inventors: Keiji Takeuchi, Tokyo; Takashi Nishino; Motoyasu Odera, both of Odawara; Hisao Shimogaki, Minami-Ashigara; Tahee Negi, Fujisawa, all of Japan

[73] Assignee: Lion Corporation, Tokyo, Japan

[21] Appl. No.: 870,018

[22] Filed: Jun. 3, 1986

[30] Foreign Application Priority Data

Jun. 6, 1985 [JP] Japan .............................. 60-123021
Jun. 6, 1985 [JP] Japan .............................. 60-123022
Dec. 20, 1985 [JP] Japan .............................. 60-286944

[51] Int. Cl.$^4$ .................... C12N 9/54; C12N 1/20; C12N 9/50; C12N 9/56; C12N 9/52
[52] U.S. Cl. ............................ 435/221; 435/219; 435/220; 435/222; 435/252.5
[58] Field of Search .............. 435/221, 222, 219, 220, 435/223, 225, 253

[56] References Cited

U.S. PATENT DOCUMENTS

| | | | |
|---|---|---|---|
| 3,674,643 | 7/1972 | Aunstrup et al. | 435/221 |
| 4,002,572 | 1/1977 | te Nijeuhuis | 435/221 X |
| 4,052,262 | 10/1977 | Horikoshi et al. | 435/221 |
| 4,480,037 | 10/1984 | Ichishima et al. | 435/221 |

FOREIGN PATENT DOCUMENTS 28537 5/1984 Australia .

Primary Examiner—Thomas G. Wiseman
Assistant Examiner—Charles L. Patterson, Jr.
Attorney, Agent, or Firm—Burns, Doane, Swecker & Mathis

[57] ABSTRACT

Novel microorganisms are provided which belong to the genus Bacillus and have ability of producing novel alkaline proteases. The alkaline proteases have excellent stability in highly alkaline conditions when blended with detergents, and improve detergency of the detergents. A process for the production of such alkaline proteases is also provided wherein the novel microorganisms are cultured.

11 Claims, 23 Drawing Sheets

FIG. I

FIG. 4
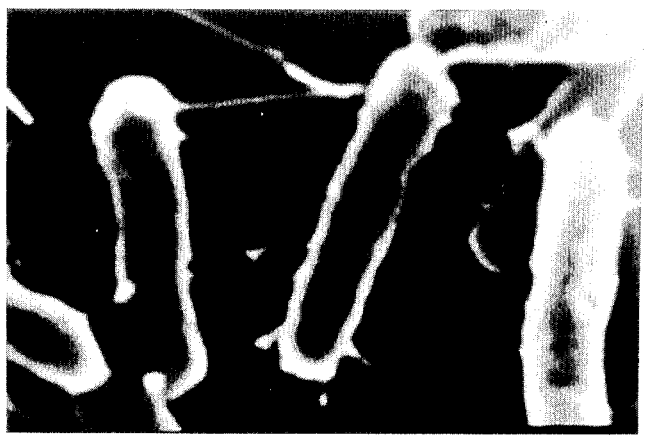
STRAIN Y ⊢――⊣ 1 μm
SPORE OF STRAIN Y ⊢――⊣ 1 μm

FIG. 5
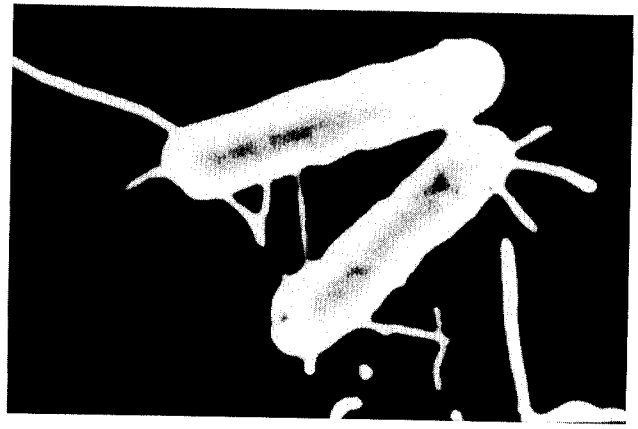
STRAIN P          ⊢——⊣ 1 μm
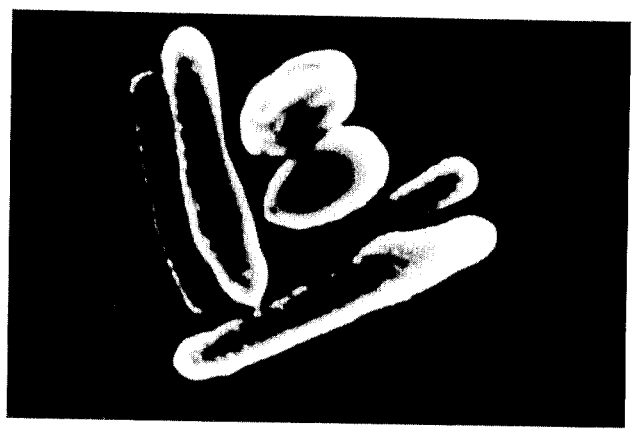
SPORE OF STRAIN P          ⊢——⊣ 2 μm FIG. 6
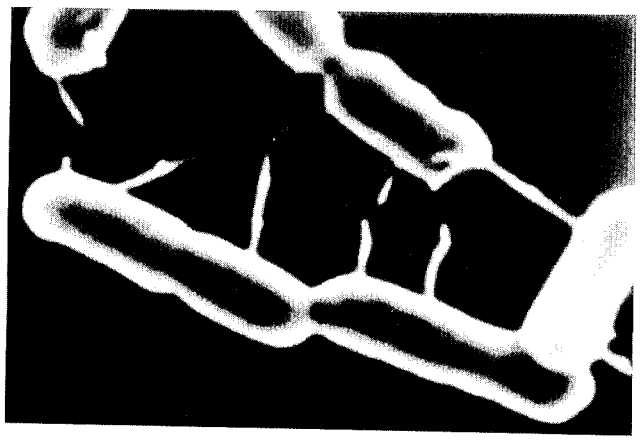
STRAIN K ⊢─────┥ 1 μm
SPORE OF STRAIN K ⊢─────┥ 2 μm

FIG. 7
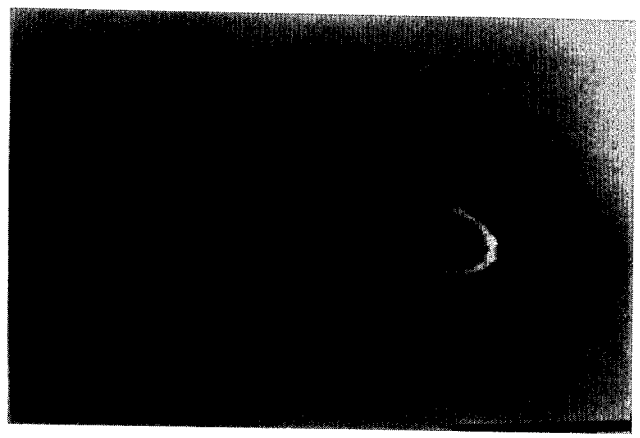
STRAIN X     |—1μm—|
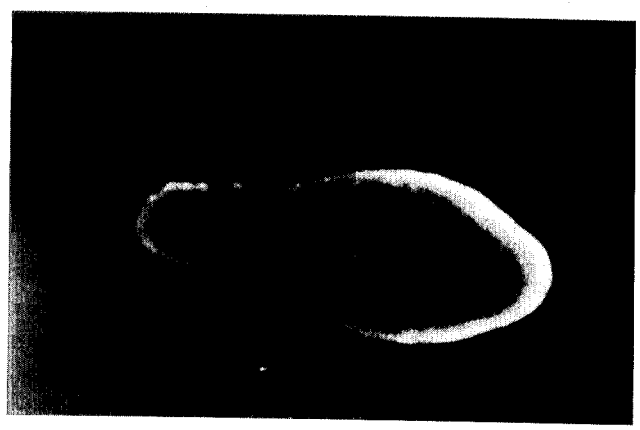
SPORE OF STRAIN X     |—1μm—|

FIG. 10
(1) OPTIMAL pH
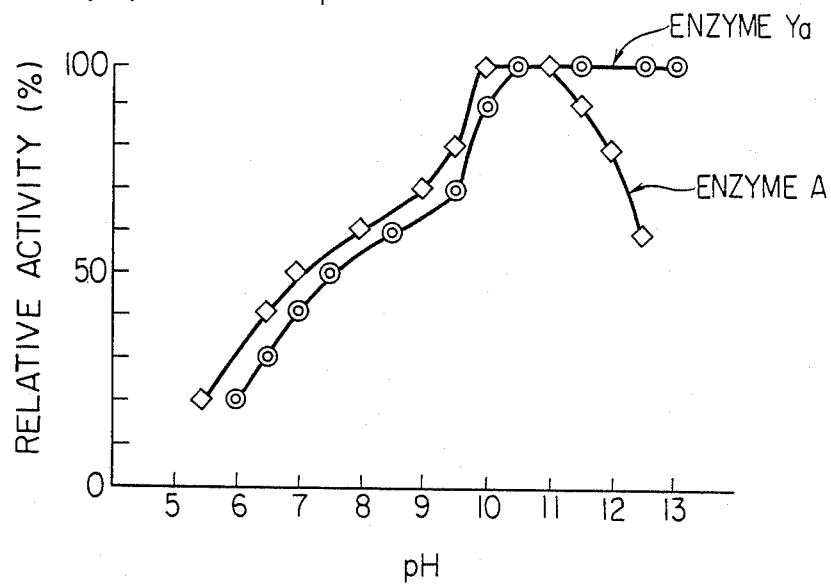
(2) pH RANGE FOR STABILITY
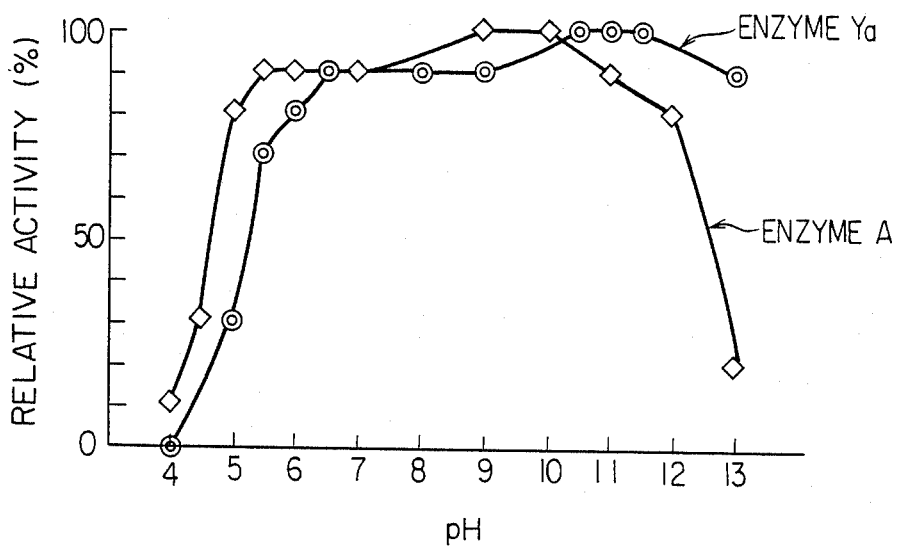

FIG. 11
(1) OPTIMAL pH
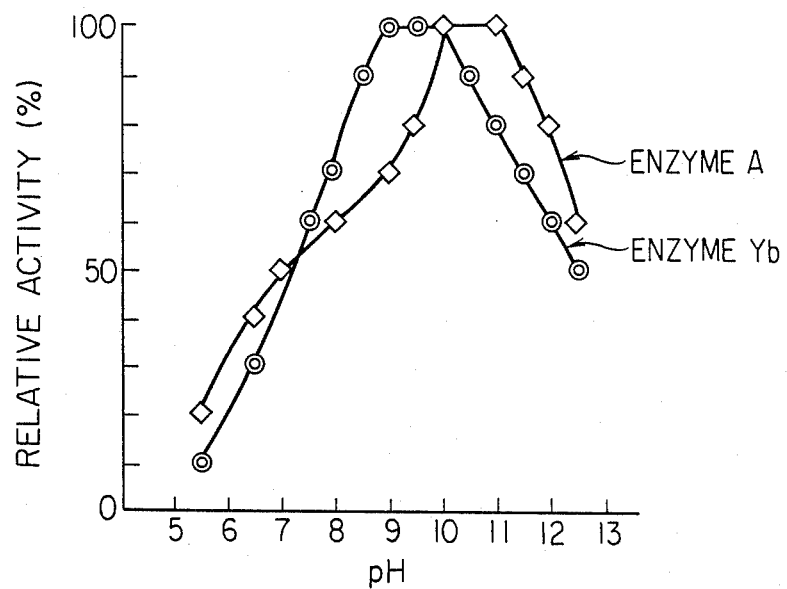
(2) pH RANGE FOR STABILITY
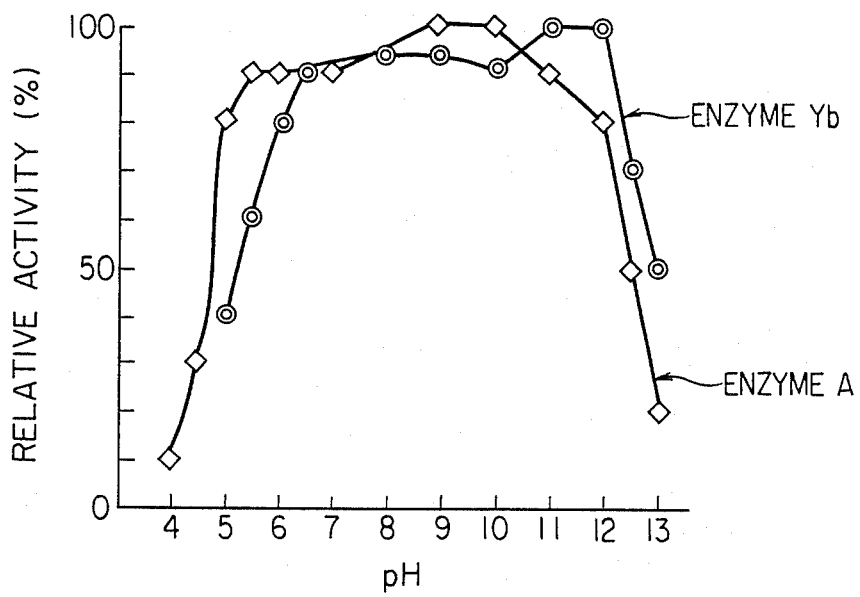

FIG. 12
(1) OPTIMAL TEMPERATURE
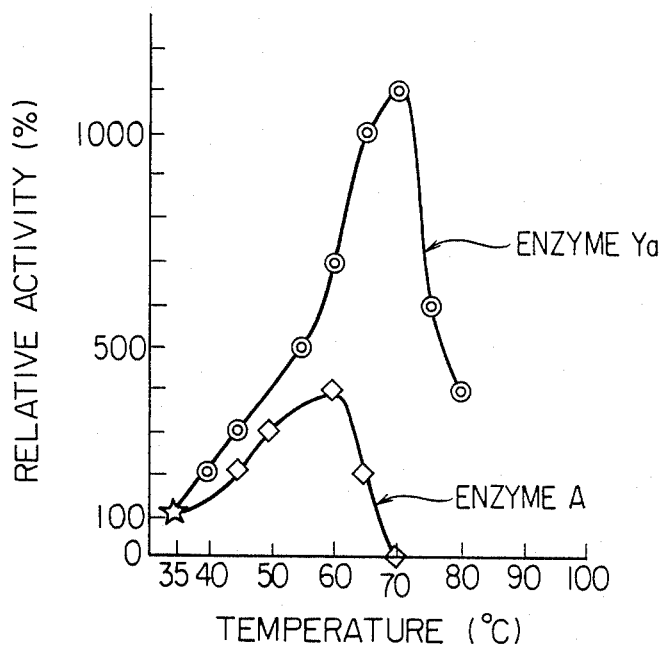
(2) THERMAL STABILITY
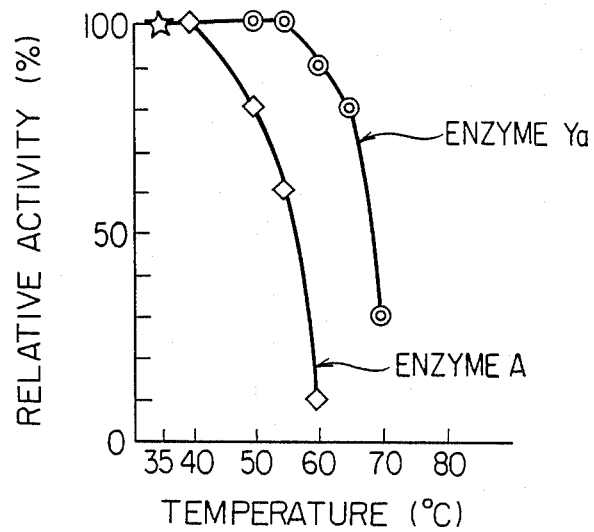

FIG. 13
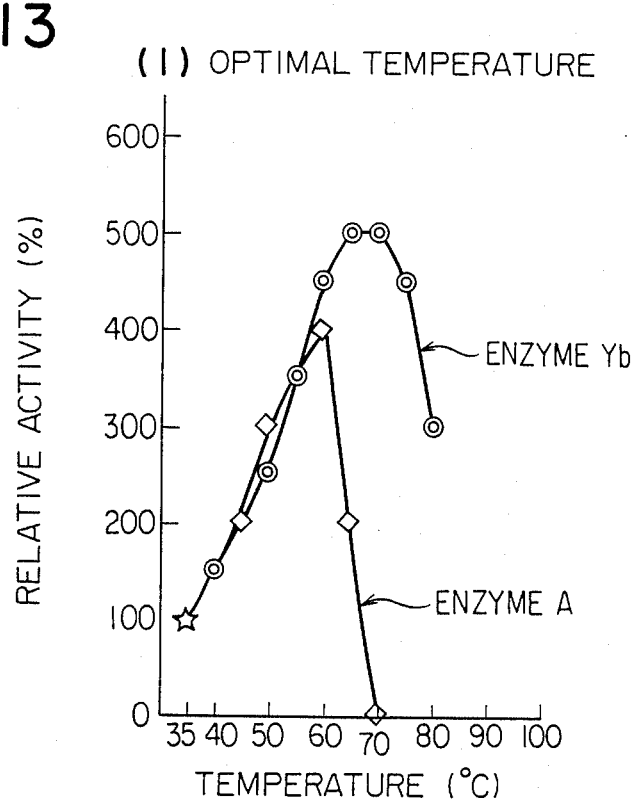
(1) OPTIMAL TEMPERATURE
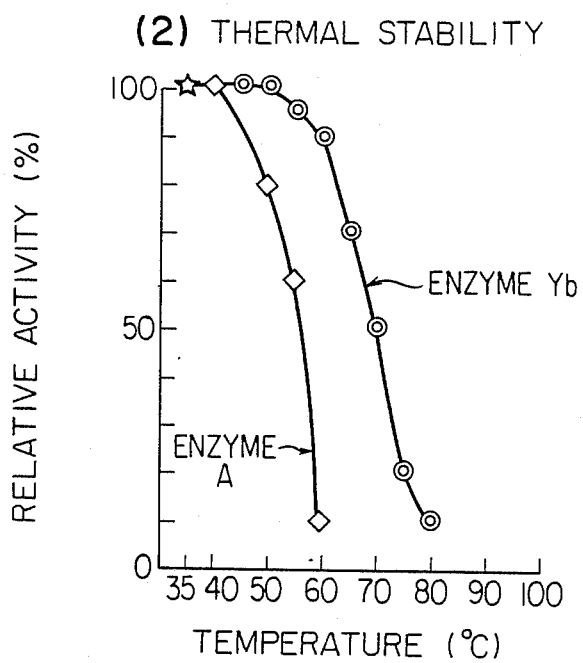
(2) THERMAL STABILITY

ALKALINE PROTEASES AND MICROORGANISMS PRODUCING SAME

BACKGROUND OF THE INVENTION (1) Field of the Invention

The present invention relates to novel alkaline proteases, particularly novel alkaline proteases which have excellent stability and contribute to improving washing ability when blended in general detergents, novel microorganisms which belong to the genus Bacillus and have an ability of producing the above proteases, a process for the preparation of the above alkaline proteases which is characterized by cultivating the above microorganisms and recovering the alkaline proteases from the culture, and detergents comprising at least one of the above alkaline proteases.

(2) Description of the Prior Art

Recently, attempts have been made to increase the washing ability of detergents, particularly of heavy duty liquid detergents, by making the pH of concentrated detergents more alkaline and blending in various hydrolytic enzymes such as proteases, amylases, lipases and cellulases. Among these enzymes, proteolytic enzyme, particularly alkaline protease, decomposes protein stains which are difficult to wash out only by a detergent, and contributes to improving washing ability. To this end, it is essential to add such an enzyme to a detergent.

Generally, alkaline protease which is produced by Bacillus licheniformis, such as those available under the trade name Alcalase (hereinafter referred to as Enzyme A), Novo Industri A/S, and the trade name Maxatase, Gist Brocades N.V., are often used. These enzymes have an optimal pH for activity of from 10 to 11, and therefore it is expected that they will exhibit their performance under a higher alkaline pH condition and contribute to the improvement of washing ability. However these enzymes immediately lose their activity in a high pH (i.e. 10 to 11) solution of a detergent, and therefore are difficult to stably blend in a heavy duty liquid detergent.

Accordingly, many attempts have been made to stabilize the activity of the enzymes in a heavy duty liquid detergent by, for example, the use of a particular anionic surfactant such as α-olefin sulfonate (Japanese Patent Publication No. (examined) 30646/1973), combination of a nitrogen compound with a lower carboxylic acid salt (Japanese Patent Publication No. (unexamined) 3733/1972), combination of free calcium ion with a polyacid for suitably chelating the calcium ion (Japanese Patent Publication No. (unexamined) 128904/1977), addition of a specific alkoxyalkylamine (Japanese Patent Publication No. (unexamined) 16012/1978), addition of a specific boric acid compound (Japanese Patent Publications Nos. (unexamined) 57209/1978 and 56204/1978), and combination of an antioxidant with a polyol (Japanese Patent Publication No. (unexamined) 27378/1980).

However, the above mentioned additives cannot sufficiently bring out the washing ability of the enzymes, though they can give to some extent a stabilization effect of the enzyme activity. Further, when a builder is blended, the enzyme activity is deteriorated and when stored at a temperature of 40° C. or more, the additives can no longer easily produce a sufficient stabilizing effect on the enzyme, and further they may harm the physicochemical stability (color, viscosity, smell, precipitate, etc.) of the heavy duty liquid detergent, and therefore further improvement is required from the practical point of view.

Another alkaline protease which is relatively stable in a high pH solution of a detergent and available under the trade name Esperase, Novo Industri A/S is also known but it cannot give sufficient washing ability even when it is used in a large amount.

Further, alkaline proteases produced by such microorganisms as *Bacillus subtilis, Bacillus alcalophilus,* Streptomyces, Aspergillus, Arthrobacter and Fusarium are also known. These proteases also have a problem in stability and washing ability as mentioned above, and therefore cannot be utilized.

Under these circumstances, it has been very difficult to further improve the washing ability of heavy duty liquid detergents.

SUMMARY OF THE INVENTION

The present invention provides novel alkaline proteases which have excellent stability in highly alkaline conditions in the presence of detergent constituents and contribute to improving washing ability.

Further, the present invention provides novel microorganisms which product the above proteases.

The present invention also provides a process for the production of the above novel alkaline proteases by cultivating the above microorganisms.

Still further, the present invention provides a detergent comprising at least one of the above novel alkaline proteases.

The present inventors investigated various natural sources in search of bacteria which produce alkaline proteases which have good stability in highly alkaline conditions in the presence of detergent constituents and contribute to improving washing ability, and have found that strain Y, strain P, strain K and strain X, all of which belong to the genus Bacillus, produce alkaline proteases which have better properties than known alkaline proteases. This finding has led to the completion of the present invention.

BRIEF DESCRIPTION OF THE FIGURES

FIG. 4 shows electron microscopic photographs of strain Y and its spore.

FIG. 5 shows electron microscopic photographs of strain P and its spore.

FIG. 6 shows electron microscopic photographs of strain K and its spore.

FIG. 7 shows electron microscopic photographs of strain X and its spore.

FIGS. 10 and 11 are graphs which show optimal pH and a pH range for stability of enzyme Ya and enzyme Yb, respectively.

FIGS. 12 and 13 are graphs which show optimal temperature and thermal stability of enzyme Ya and enzyme Yb, respectively.

Figure 1:
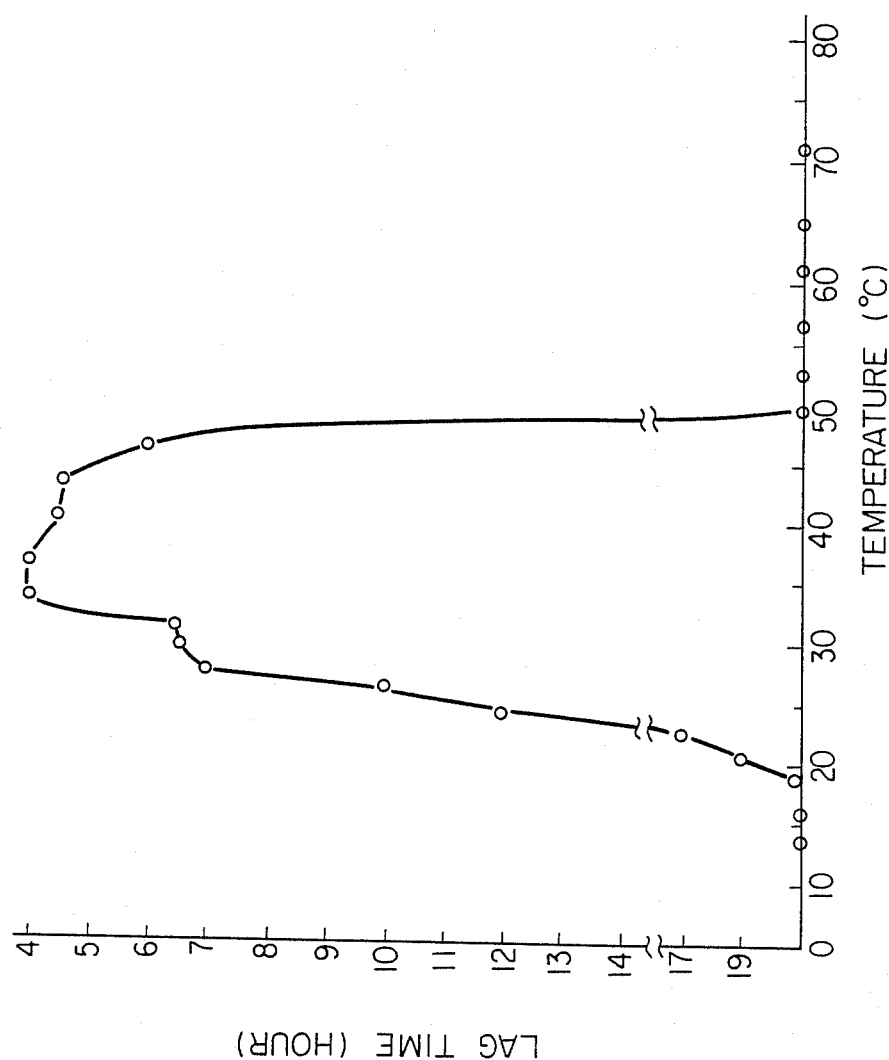
FIG. 1 is a graph which shows growth temperatures of the present bacterial strains.

DETAILED DESCRIPTION OF THE INVENTION (1) Novel microorganisms

The novel microorganisms according to the present invention belong to the genus Bacillus and produce novel proteases which have excellent stability in highly alkaline conditions in the co-existence of detergent constituents and contribute to improving washing ability. As examples, there can be mentioned Bacillus sp Y, P, K and X. these microorganisms were deposited on Feb. 13, 1985 with the Fermentation Research Institute, Agency of Industrial Science and Technology, Ministry of International Trade and Industry, Japan, International Depository Authority (hereinafter referred to as "FERM"). The deposit numbers are as follows;

Bacillus sp. Y: FERM BP - 1029
Bacillus sp. P: FERM BP - 1030
Bacillus sp. K: FERM BP - 1031
Bacillus sp. X: FERM BP - 1032

Microbiological properties of the present strains isolated from the natural field by the present inventors will be explained below in detail.

Determination of microbiological properties and classification were conducted according to the reference table of R. E. Gordon (1972), Bergey's Manual of Determinative Bacteriology, 8th edition (1974). Media of pH 10 were prepared by adding 1% sodium carbonate. Determination of optimal ranges for growth of temperature and pH were carried out by a temperature-gradient biophotorecorder.

A. Morphological properties

The following morphological properties are observed under culturing on a nutrient agar medium at 35° C. for 2 days.

(1) Shape and size of cells: all of the strains are rods, the sizes of which are 0.4–0.5 $\mu m \times$ 1.6–2.0 $\mu m$.
strain Y: 0.4–0.5 $\mu m \times$ 1.7–1.9 $\mu m$
strain P: 0.4–0.5 $\mu m \times$ 1.7–2.0 $\mu m$
strain K: 0.4–0.5 $\mu m \times$ 1.6–1.8 $\mu m$
strain X: 0.4–0.5 $\mu m \times$ 1.8–2.0 $\mu m$ (2) Pleomorphism: all of the strains show no pleomorphism.

(3) Motility: all of the strains have peritrichous flagella, showing motility.

(4) Spore: all of the strains form spores. Cells distend around the termini in the course of formation. Matured spores are of a lemon shape, the size of which is 0.7–1.0 $\mu m \times$ 1.0–1.8 $\mu m$.
strain Y: 0.7–0.9 $\mu m \times$ 1.0–1.2 $\mu m$
strain P: 0.8–1.0 $\mu m \times$ 1.3–1.5 $\mu m$
strain K: 0.8–1.0 $\mu m \times$ 1.5–1.8 $\mu m$
strain X: 0.9–1.0 $\mu m \times$ 1.0–1.2 $\mu m$ (5) Gram strain: all of the strains are positive.
(6) Acid-fastness: all of the strains are negative.

B. Cultural properties (1) Nutrient agar plate culture:

All strains grow at pH 7.0 to form round, flat or umbilicate, entire or undrate colonies. The surface of the colony is smooth and glossy. They grow at pH 10.0 to form round, flat and entire colonies. The surface of the colony is smooth and glossy.

strain Y: It grows at pH 7.0 to form round, flat and entire colonies. The surface of the colony is smooth and glossy. The peripheral part is pale brown and the central part is semitransparent pale brown.

It grows at pH 10.0 to form round, flat and entire colonies. The surface of the colony is smooth, glossy and cream-colored.

strain P: It grows at pH 7.0 to form round, flat and entire colonies. The surface of the colony is smooth, glossy, semitransparent and cream-colored.

It grows at pH 10.0 to form round, flat and entire colonies. The surface of the colony is smooth, glossy and cream-colored.

strain K: It grows at pH 7.0 to form round, umbilicate and undulate colonies. The surface of the colony is smooth, glossy and transparent.

It grows at pH 10.0 to form round, flat and entire colonies. The surface of the colony is smooth, glossy and cream-colored.

strain X: It grows at pH 7.0 to form round, flat and entire colonies. The surface of the colony is smooth and glossy. The peripheral part is cream-colored and the central part is pale brown.

It grows at pH 10.0 to form round, flat and entire colonies. The surface of the colony is smooth, glossy and cream-colored or pale yellow.

(2) Nutrient agar slant culture

All strains grow at pH 7.0 and pH 10.0 in a strip or a broad strip to form glossy and cream-colored or pale brown colonies.

strain Y: It grows at pH 7.0 and pH 10.0 in a broad strip form to form glossy and cream-colored or pale brown colonies. It produces a slight amount of red-brown pigment.

strain P: It grows at pH 7.0 and pH 10.0 in a strip form to form glossy, cream-colored and semitransparent colonies. No pigment is produced.

strain K: It grows at pH 7.0 in a strip form to form glossy, transparent colonies. No pigment is produced.

It grows at pH 10.0 in a broad strip form to form glossy and cream-colored colonies. No pigment is produced.

strain X: It grows at pH 7.0 and pH 10.0 in a broad strip form to form glossy and cream-colored colonies. No pigment is produced.

(3) Nutrient broth culture strains Y, P, K and X: They all grow at pH 7.0, but form no pellicle.

They grow all well at pH 10.0, but form no pellicle.

(4) Gelatin stab culture strains Y, P, K and X: All are slightly liquified at pH 7.0.

All are liquified at pH 10.0.

(5) Litmus milk strains Y, P, K and X: All grow very poorly at pH 7.0.

All grow at pH 10.0. No coagulation of milk is observed. Change in color of litmus is unknown because of alkalinity of the media.

C. Physiological properties (common in strains Y, P, K and X).

(1) Reduction of nitrate: positive.
(2) Denitrification: negative.
(3) MR test: negative.
(4) VP test: negative.
(5) Production of indole: negative.
(6) Production of hydrogen sulfide: negative
(7) Hydrolysis of starch: positive.
(8) Utilization of citric acid: it is not utilized in Koser's medium, but slightly utilized in Christensen's medium.
(9) Utilization of inorganic nitrogen sources: nitrates are not utilized; ammonium salts are not utilized.
(10) Production of pigment: no pigment is formed.
(11) Urease: positive.
(12) Oxidase: positive.
(13) Catalase: positive.
(14) Temperature range for growth: a temperature of 20° to 47° C., particularly of 33° to 35° C. is good.
(15) pH range for growth: pH of 6.0 to 12.0 particularly around 10.0 is good.
(16) Behavior to oxygen: aerobic.
(17) O–F test: negative.
(18) Production of acids and gases from saccharides: (+, produced; −, not produced).

| Saccharide | Strain Y acid | Strain Y gas | Strain P acid | Strain P gas | Strain K acid | Strain K gas | Strain X acid | Strain X gas |
|---|---|---|---|---|---|---|---|---|
| L-arabinose | − | − | − | − | − | − | − | − |
| D-xylose | − | − | − | − | − | − | − | − |
| D-glucose | + | − | + | − | + | − | + | − |
| D-mannose | + | − | + | − | + | − | + | − |
| D-fructose | + | − | + | − | + | − | + | − |
| D-galactose | − | − | − | − | − | − | − | − |
| maltose | + | − | + | − | + | − | + | − |
| sucrose | + | − | + | − | + | − | + | − |
| lactose | − | − | − | − | − | − | − | − |
| trehalose | + | − | + | − | + | − | + | − |
| D-sorbitol | − | − | − | − | − | − | − | − |
| D-mannitol | + | − | + | − | + | − | + | − |
| inositol | − | − | − | − | − | − | − | − |
| glycerol | − | − | − | − | − | − | − | − |
| starch | + | − | + | − | + | − | + | − |

D. Other properties (1) Resistance to sodium chloride: all of the strains grow in 10% NaCl.

(2) Strains Y, P, K and X produce alkaline proteases which have an optimal pH of 9 or higher and excellent stability in alkaline conditions in the co-existence of detergent constituents and contribute to improving washing ability.

Summarizing the above properties, first the present strains are Gram positive rods which are catalase positive, are aerobic and produce heat-resistant endospores. Thus, they belong to the genus Bacillus.

Further, the present strains are rods having peritrichous flagella. In the course of formation of spores, the cells distend at a position around the termini. Matured spores are of a lemon shape.

FIG. 4 shows electron microscopic photographs of strain Y and its spore.

FIG. 5 shows electron microscopic photographs of strain P and its spore.

FIG. 6 shows electron microscopic photographs of strain K and its spore.

FIG. 7 shows electron microscopic photographs of strain X and its spore.

The present strains are mesophile, cannot grow at a temperature below 20° C. or above 50° C. and have an optimal growth temperature of around 33° to 35° C. (see FIG. 1).

Figure 2:
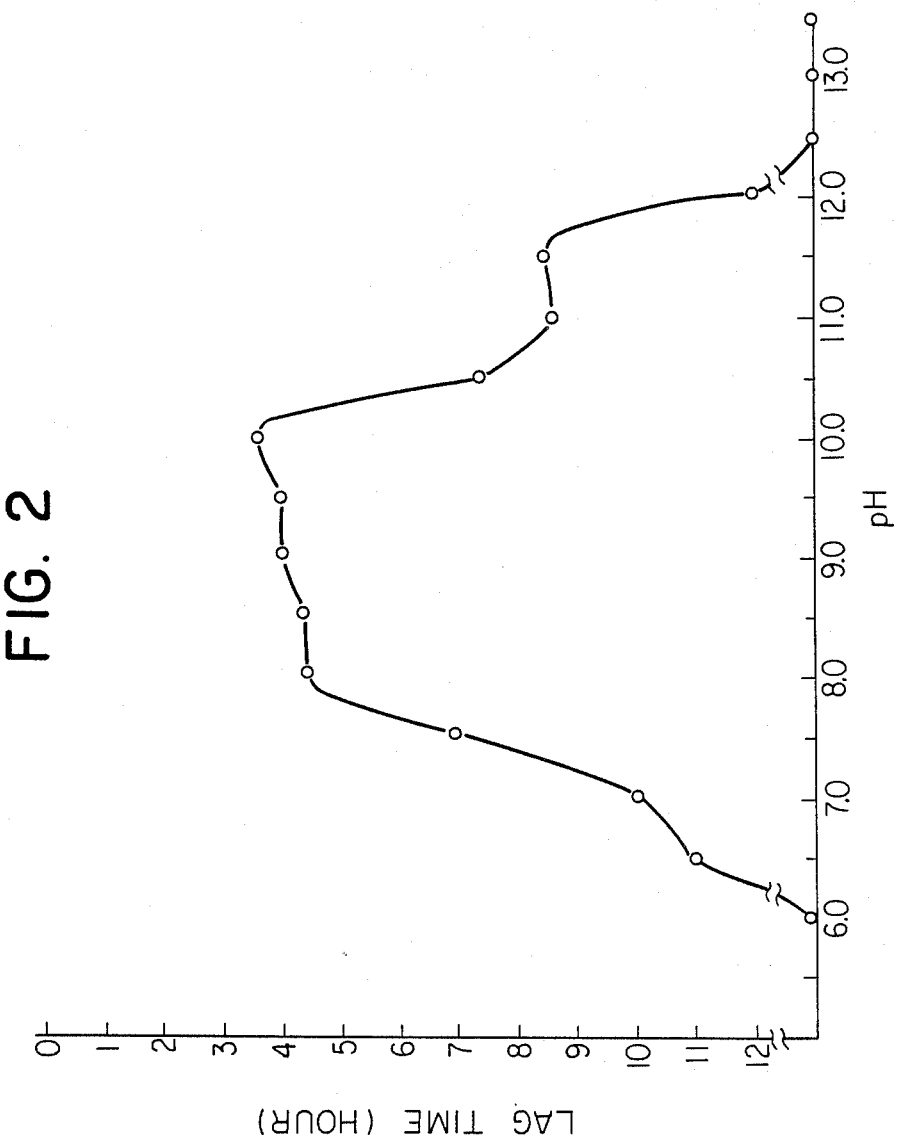
FIG. 2 is a graph which shows growth pHs of the present bacterial strains.

Further, the present strains are alkalophile, cannot grow at a pH below 6 or above 12.5 and have an optimal growth pH of around 10.0 (see FIG. 2).

The present strains have a property of producing acids from aldohexoses among monosaccharides, from disaccharides other than lactose, and fromonly mannitol among sugar alcohols. They do not produce gas.

As known strains having similar microbiological properties to the present strains, there may be mentioned *Bacillus pasteurii* and *Bacillus alcalophilus*. The present strains are different from *Bacillus pasteurii* in that the former hydrolyze starch, while the latter does not, and the former do not require ammonium salts for propagation in an alkaline medium, while the latter does.

Further, the present strains form endospore of lemon shape, while *Bacillus pasteurii* forms endospore of spherical or elliptical shape. From the above differences in the microbiological properties, the present strains are clearly distinguished from *Bacillus pasteurii*.

Further, as the present strains seemed to belong to *Bacillus alcalophilus*, they were compared with *Bacillus alcalophilus* NCTC 4553 (ATCC 27647) which is an original strain as described in Bergey's Manual of Determinative Bacteriology, 8th edition. The present strains differ from NTCC 4553 strain in that the former reduce nitrates, while the latter does not, and the former do not decolorize methylene blue, while the latter does.

Further, the present strains were compared in detail with Alkalophilic Bacillus sp. No. 221 (ATCC 21522), No. 58 (Japanese Patent Publications (examined) 2792/1973 and 16435/1975) and No. D-6 (Japanese Patent Publication (examined) 4236/1981 (Horikoshi et al., The Institute of Physical and Chemical Research) for microbiological properties. The present strains and Bacillus sp. No. 221, No. 58 and No. D-6 share a common property that they grow well on an alkaline medium (pH 10). However, the present strains cannot utilize nitrates or ammonium salts, while the above known strains can utilize these salts. Further, the present strains have a growth pH range of from 6 to 12, while that of No. 221 is from 7 to 11 and those of No. 58 and No. D-6 are from 7.5 to 11. Thus, the above known strains cannot grow at a pH below 7.0. Regarding temperatures for growth, the present strains have a growth temperature range of from 20° to 47° C. and an optimal temperature range of 33° to 35° C. No. 221 can grow at temperatures up to 55° C. and No. 58 up to 45° C. and their optimal temperature range is 37° C. to 40° C. No. D-6 shows a high optimal temperature range of from 35° to 40° C., which differs from those of the present strains. Comparing the present strains with No. D-6 for acids production from saccharides, the present strains do not produce acids from L-arabinose, D-xylose, D- galactose or glyceral, but No. D-6 does. Furthermore, the present strains grow in 10% NaCl conditions, which also distinguish them from the above known strains.

The above results are summarized in Table 1 below. Since the present strains are obviously different from the known strains *Bacillus pasteurii* and *Bacillus alcalophilus* having the similar microbiological properties thereto, it is appropriate to decide that the present strains are new strains which belong to the genus Bacillus. Thus, the inventors of this invention concluded that the present strains are new and named them Bacillus sp. Y, P, K and X, respectively.

TABLE 1

| Microbiological property | Strains Y,P,K and X | No. 221 | No. 58 | No. D-6 |
|---|---|---|---|---|
| Size of Cell | 0.40–0.50 × 1.6–2.0 μm | 0.6–0.9 × 1.5–2 μm | 0.6–0.8 × 2–3 μm | 0.5–0.7 × 2–4 μm |
| VP Test | — | — | + | — |
| Utilization of Inorganic Nitrogen Sources (Ammonium salt) | no | yes | yes | slightly |
| Growth Temperature Range | 20–47° C. | −55° C. | −45° C. | — |
| Optimal Temperature Range | 33–35° C. | 37–40° C. | 37–40° C. | 35–40° C. |
| Growth pH Range | 6–12 | 7–11 | 7.5–11 | 7.5–11 |
| Optimal pH Range | around 10 | around 10 | around 10 | around 10 |
| Saccharides as Sources for Acid Production | glucose mannose fructose maltose sucrose trehalose mannitol starch | | | In addition to those described left, arabinose xylose galactose glycerol |
| Resistance to NaCl | grow in 10% NaCl | grows little in 5% NaCl | grows in 7% NaCl | grows in 5% NaCl |

(2) Preparation of novel alkaline proteases

Figure 8:
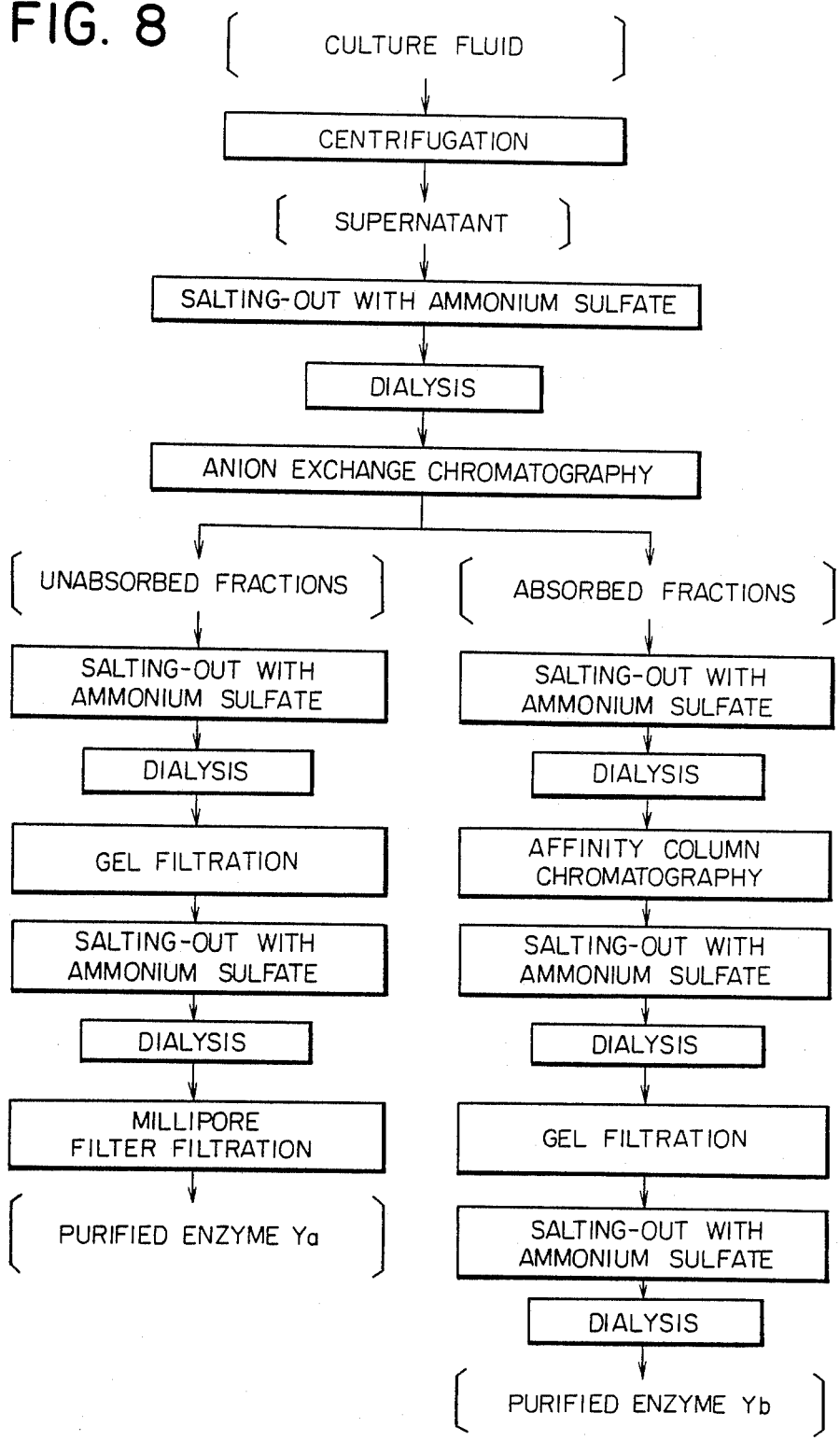
FIG. 8 is a flow sheet which shows a purification process of the present enzymes.

The alkaline proteases according to the present invention may be prepared by cultivating the novel microorganisms of the invention, and isolated and purified by such a method as described in FIG. 8.

For cultivating the present strains, it is possible to use any culture media, solid or liquid, which is usable for conventional cultivation of microorganisms and which can be utilized by the present strains. Such culture media contain an alkaline buffer as well as components necessary for the microorganisms to grow such as a carbon source, a nitrogen source, an inorganic salt, etc. and have a pH of 8 to 11.

Examples of carbon sources include mannose, fructose, mannitol, maltose, cellobiose, sucrose, dextrin, starch, molasses, etc. Examples of nitrogen sources include soybean flour, soybean casein, defatted soybean flour, corn steep liquor, dried yeast, yeast extract, etc. Examples of inorganic salts include potassium phosphate, magnesium sulfate, etc. Examples of alkaline buffers include sodium carbonate, potassium carbonate, sodium bicarbonate, sodium phosphate, sodium tetraborate, glycine, etc. If desired, there can be added other various organic or inorganic substances necessary for the growth of the microorganisms or the production of the enzymes.

The media containing the above mentioned components are sterilized in a conventional manner and inoculated with the present strain. Cultivation may be conducted aerobically with shaking or under aerated agitation at 30° to 37° C. for 40 to 150 hours to obtain a culture fluid. After the cells are removed, the supernatant is subjected to one or more processes such as conventional salting out, precipitation by the addition of an organic solvent, isoelectric point precipitation, ultrafiltration, condensation under reduced pressure, ion-exchange or gel filtration, to collect crude or purified enzymes in the form of powder or concentrated liquid.

The novel microorganism of the present invention, Bacillus sp. Y, produces two kinds of alkaline proteases, that is, enzyme Ya and enzyme Yb. Isolation and purification of the alkaline proteases may be carried out by a method as shown in FIG. 8. That is, a microorganism culture fluid is centrifuged, for instance, at 10,000 rpm for 5 minutes to obtain a supernatent. The supernatent is subjected to 70% saturated ammonium sulfate salting-out. Precipitates are dissolved in a buffer solution, which is then dialysed against the same buffer. The solution is subjected to anion exchange chromatography and unabsorbed fractions are collected to obtain crude fractions of enzyme Ya. The unabsorbed fractions are again subjected to ammonium sulfate precipitation, dialysis and gel filtration, and active fractions are collected. Those are further subjected to ammonium sulfate precipitation and dialysis, and are filtered to obtain purified enzyme Ya.

Figure 9:
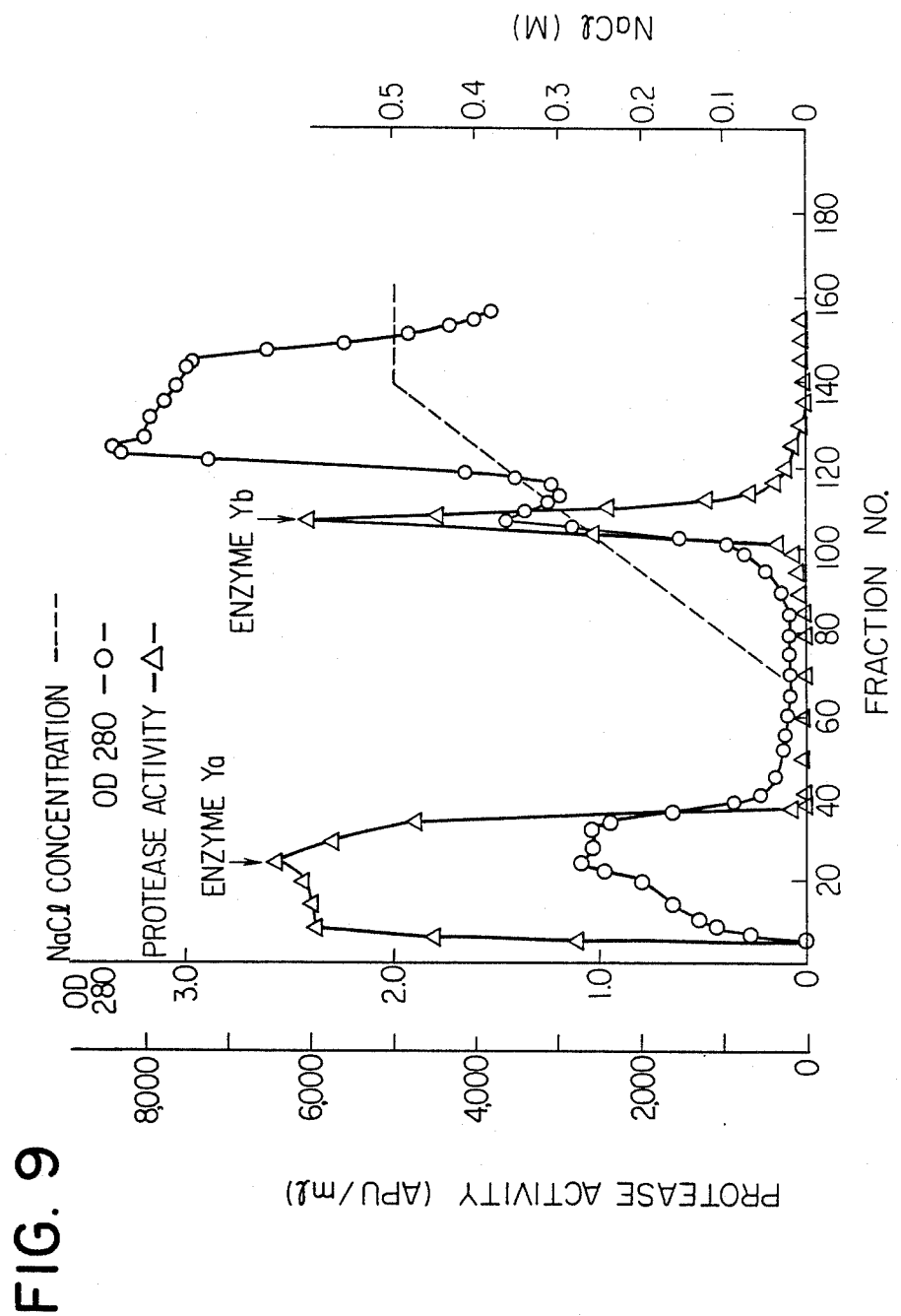
FIG. 9 is a graph which shows elution patterns of the present enzymes on a DEAE-53 cellulose column chromatography.

Meanwhile, the fractions absorbed in the course of the above anion exchange chromatography are eluted with a linear gradient of 0 to 0.5 M NaCl in a buffer solution to obtain active fractions of enzyme Yb. FIG. 9 shows an elution pattern of anion exchange chromatography.

The active fractions of enzyme Yb are again subjected to ammonium sulfate precipitation and dialysed against a buffer solution. Then, the solution is subjected to affinity chromatography to collect active fractions, which are then subjected to ammonium sulfate precipitation and dialysed against the buffer solution. The solution is further subjected to gel filtration and eluted by the buffer solution to collect active fractions, which are then subjected to ammonium sulfate precipitation. Precipitates are dialysed against the buffer solution to obtain purified enzyme Yb.

(3) Physicochemical properties of novel alkaline proteases

Physicochemical properties of enzyme Ya and enzyme Yb thus obtained are as follows:

(i) Substrate specificity

Substrate specificities of Ya, Yb and a mixture of Ya and Yb (1:1) are shown in Table 2 in comparison with that of enzyme A.

TABLE 2*

| Enzyme | Substrate | | | |
|---|---|---|---|---|
| | Keratin | Hemoglobin | Egg Albumen | Egg Yolk |
| Enzyme A | 100 | 100 | 100 | 100 |
| Enzyme Ya | 187 | 99 | 28 | 82 |
| Enzyme Yb | 42 | 107 | 290 | 130 |
| Ya/Yb = 1/1 | 131 | 110 | 390 | 160 |

*Relative activity on a basis of the activity of enzyme A at 100

Conditions: reaction temperature 35° C.; pH 10.5 (50 mM borate-NaOH buffer) reaction time 60 minutes; concentration of a substrate 1% with the exception of hemoglobin (0.4%); used amount of enzyme 100 APU/ml with the exception of egg albumen (500 APU/ml).

Protein decomposition rates, i.e., activity, were measured according to a modified Anson-Hagiwara method. Absorbances of the reaction solutions filtered after the reaction were measured at 275 nm. Enzyme activity which releases 1 µg of tyrosine per minute is designated one (1) alkaline protease unit (APU).

It is clear from the above table that enzyme Ya shows strong specificity to keratin and enzyme Yb shows strong specificity to egg albumen, egg yolk and hemoglobin. A combination of both enzymes acts strongly on a wider range of substrates, compared to known enzyme A.

(ii) Optimal pH and pH range for stability

FIGS. 10 and 11 show the optimal pHs and pH ranges for stability of enzyme Ya and enzyme Yb. Used buffer solutions are as follows:

| pH Range | Buffer |
|---|---|
| 3.5–5.5 | Sodium acetate acetic acid |
| 4.5–7.0 | citric acid-Na$_2$HPO$_4$ |
| 6.0–8.0 | NaH$_2$PO$_4$—Na$_2$HPO$_4$ |
| 7.5–9.0 | Tris-HCl |
| 8.0–9.0 | borate-HCl |
| 9.0–10.5 | glycine-NaOH |
| 9.5–11.0 | borate-NaOH |
| 11.0–12.0 | Na$_2$HPO$_4$—NaOH |
| 12.0–13.0 | KCl—NaOH |

When optimal pH was examined, each enzyme was added to each 20 mM buffer solution containing 0.6% casein, and reacted at 35° C. for 10 minutes, and then absorbance was measured at 275 mm. Relative activity at each pH was calculated based on the activity at the optimal pH (at 100). When a pH range for stability was examined, each enzyme was added to each 20 mM buffer solution at a final concentration about 400 APU/ml, and incubated at 25° C. for 24 hours, and then activity was measured. Relative activity was calculated at each pH, based on activity before incubation (at 100). As seen from FIG. 10, the optimal pH of enzyme Ya is 10.0 to 12.5 and the pH range for stability is 6.5 to 13.0. As seen from FIG. 11, the optimal pH of enzyme Yb is 9.0 to 10.0 and the pH range for stability is 6.5 to 12.0.

(iii) Optimal temperature and thermal stability

FIGS. 12 and 13 show the optimal temperatures and thermal stability of enzyme Ya and enzyme Yb. When the optimal temperature was examined, each enzyme was added to a buffer solution of pH 10.5 containing 0.6% casein as a substrate and reacted at each given temperature for 10 minutes. Relative activity at each temperature, based on activity at 35° C. (at 100), was obtained. The thermal stability was examined as follows. Each enzyme, at about 400 APU/ml (final concentration), was added to a 50 mM borate-NaOH buffer solution (pH 10.5 at 35° C.), incubated at each temperature for 10 minutes and ice-cooled, and, then, the absorbance was measured. As seen from FIG. 12, the optimal temperature of enzyme Ya is 70° C. and the activity thereof is maintained up to 55° C.. As seen from FIG. 13, the optimal temperature of enzyme Yb ranges from 65° to 70° C., and the activity thereof is fully maintained up to 50° C.

(iv) UV absorption spectrum

Figure 14:
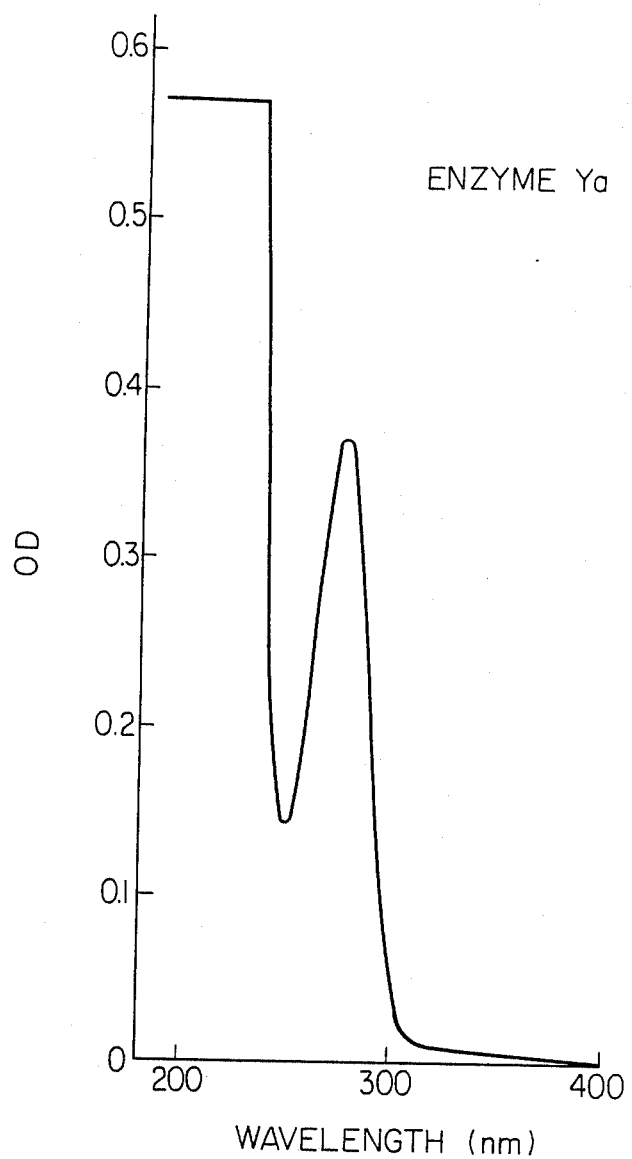
FIGS. 14 and 15 are graphs which show a UV absorption spectrum of enzyme Ya and enzyme Yb, respectively.
Figure 15:
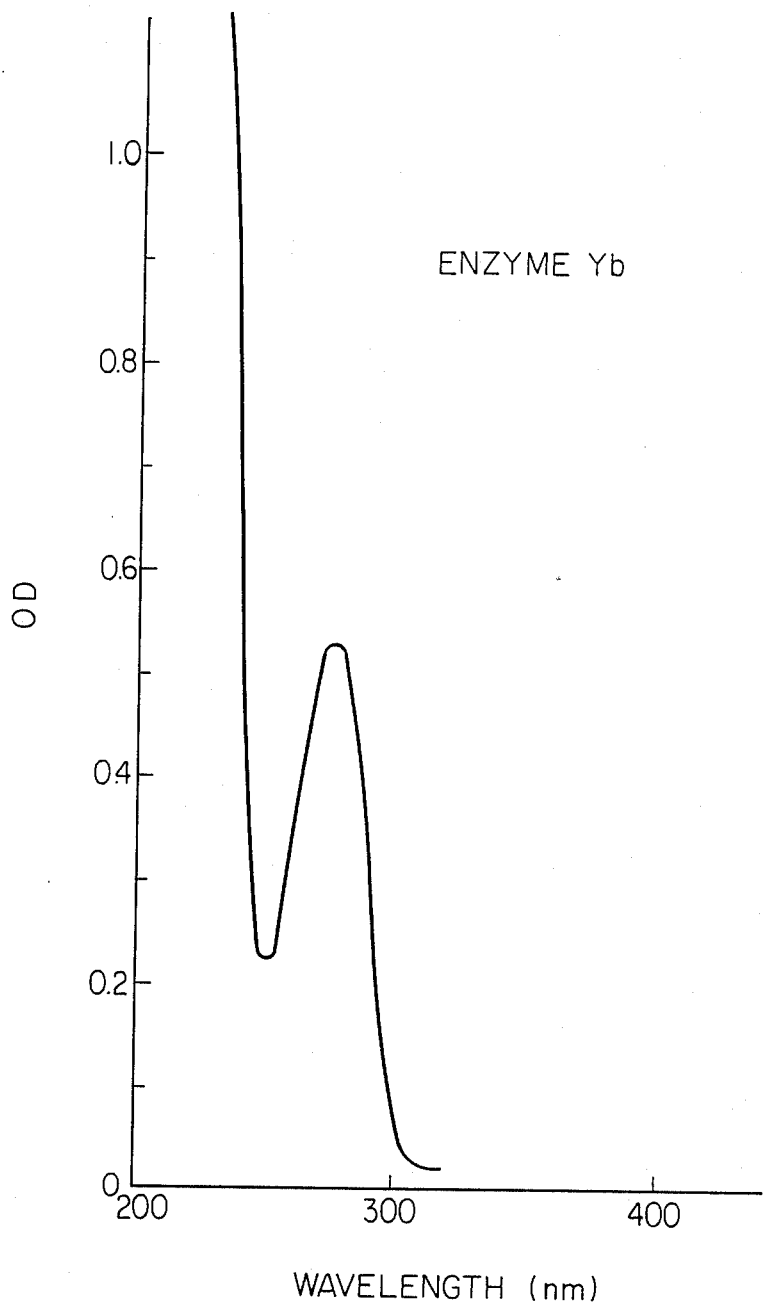

FIGS. 14 and 15 show UV absorption spectra of enzyme Ya and enzyme Yb. Each sample was dissolved in a 50 mM Tris-HCl buffer solution (pH 8.0) and its UV absorption spectra were measured. Absorption peaks of Ya and Yb were observed at 276 nm and 278 nm, respectively. Extinction coefficients at these wavelengths, $E_1$ 1% cm, were calculated as 7.5 and 9.5, respectively.

(v) Effect of metal ions

Effect of metal ions on the activity of enzyme Ya and enzyme Yb was determined. Casein was used as a substrate. The results are shown in Tables 3 and 4, respectively. Each metal ion was added in a final concentration of 1mM to a 20 mM borate-NaOH buffer solution (pH 10.5) containing enzyme Ya or enzyme Yb (final concentration, about 400 APU/ml). After treatment under given conditions, the remaining activity was measured. The values are expressed in relative activity on the basis of the activity at the time of zero minute (at 100).

TABLE 3

| Metal Salts | Condition | | |
|---|---|---|---|
| | 25° C. 60 Min. | 40° C. 60 Min. | 40° C. 24 Hours |
| — | 99 | 98 | 85 |
| NaCl | 100 | 100 | 91 |
| KCl | 98 | 98 | 85 |
| LiCl | 100 | 100 | 86 |
| CoCl$_2$ | 100 | 100 | 91 |
| NiCl$_2$ | 100 | 100 | 91 |
| BaCl$_2$ | 100 | 100 | 92 |
| FeSO$_4$ | 100 | 99 | 79 |
| CaCl$_2$ | 100 | 100 | 96 |
| CuSO$_4$ | 86 | 74 | 26 |
| MgSO$_4$ | 100 | 100 | 89 |
| Na$_2$SO$_4$ | 100 | 100 | 90 |
| MnCl$_2$ | 100 | 100 | 80 |
| AgNO$_3$ | 87 | 80 | 6 |
| HgCl$_2$ | 22 | 18 | 2 |
| CdCl$_2$ | 81 | 81 | 75 |
| ZnCl$_2$ | 100 | 97 | 85 |

As seen from the above table, the activity of enzyme Ya was inhibited by the addition of copper sulfate, silver nitrate, mercuric chloride, and cadmium chloride.

TABLE 4

| Metal Salts | Condition | |
|---|---|---|
| | 35° C. 30 Min. | 35° 17 Hours |
| HgCl$_2$ | 64 | 34 |
| CuSO$_4$ | 80 | 62 |
| FeSO$_4$ | 100 | 99 |
| ZnCl$_2$ | 100 | 100 |
| AgNO$_3$ | 100 | 62 |
| — | 100 | 100 |

This table shows that the activity of enzyme Yb was inhibited by the addition of copper sulfate, silver nitrate, and mercuric chloride.

Generally, thermal stability of alkaline proteases produced by bacteria belonging to the genus Bacillus are increased by $Ca^{2+}$ ion. Accordingly, in order to observe the effect of $Ca^{2+}$ ion, about 400 APU/ml (final concentration) of each of enzyme Ya and enzyme Yb was added to a 50 mM borate-NaOH buffer solution (pH 10.5 at 35° C.) with or without containing 5 mM $Ca^{2+}$ ion and incubated at respective given temperatures for 10 minutes and cooled on ice, and thereafter the activity was measured. The results are shown in Table 5. The values are expressed in relative activity on the basis of the activity at the time of zero minute (at 100).

TABLE 5

| Temperature | enzyme Ya | | enzyme Yb | |
|---|---|---|---|---|
| | none | 5 mMCa$^{2+}$ | none | 5 mMCa$^{2+}$ |
| 35° C. | 100 | 100 | 100 | 100 |
| 40 | 100 | 100 | 100 | 100 |
| 50 | 100 | 100 | 100 | 100 |
| 55 | 100 | 100 | 96 | 100 |
| 60 | 92 | 100 | 90 | 100 |
| 65 | 75 | 90 | 72 | 92 |
| 70 | 22 | 57 | 45 | 75 |

It can be seen that the thermal stability was increased by about 5° C. for enzyme Ya and about 10° C. for enzyme Yb by the addition of $Ca^{2+}$ ion.

(iv) Effects of various inhibitors

Effects of various inhibitors on enzyme Ya and enzyme Yb were determined. Enzyme Ya was added to a 50 mM Tris-HCl buffer solution (pH 7.2) at 800 APU/ml (final concentration). Each inhibitor was added and incubated at 35° C. for 30 minutes and, then, the remaining activity was measured. The values are expressed in relative activity on the basis of the activity with no inhibitor (at 100). The results are shown in Table 6.

TABLE 6

| Inhibitor | Concentration | Relative Activity | | Note |
|---|---|---|---|---|
| | | Enzyme Ya | Enzyme Yb | |
| — | | 100 | 100 | |
| Urea | 6 M | 130 | 82 | Protein denaturant |
| EDTA | 5 mM | 97 | 100 | Metal protease inhibitor |
| DFP | 1 mM | 0 | 4 | Serine protease inhibitor |
| PMSF | 1 mM | 0 | 1 | Serine protease inhibitor |
| HgCl$_2$ | 1 mM | 106 | 96 | SH - enzyme inhibitor |
| PCMB | 1 mM | 122 | 92 | SH - enzyme inhibitor |
| Antipain | 100 g/ml | 124 | 87 | SH - enzyme inhibitor |
| Chymostatin | 100 g/ml | 77 | 75 | Ca dependent protease inhibitor |

As seen from this table, enzyme Ya and enzyme Yb are concluded that they contain serine in their active center, judging from the fact that, when casein is used as a substrate, they are not inhibited by EDTA, PCMB, antipain or chymostatin, but are inhibited by DFP and PMSF.

(vii) Effect of surfactants

Figure 16:
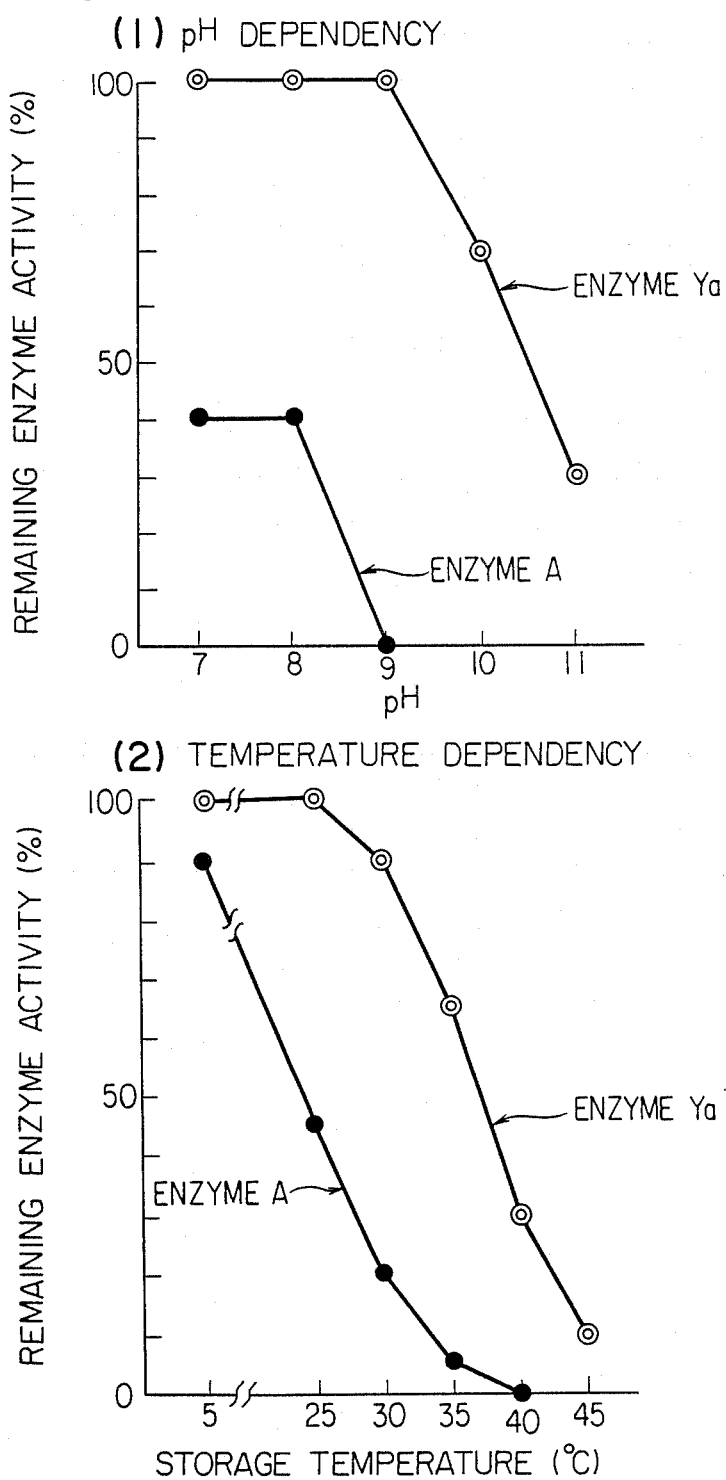
FIGS. 16 and 17 are graphs which show stability of enzyme Ya and enzyme Yb in a heavy duty liquid detergent.

Stability of enzyme Ya during storage in a heavy duty liquid detergent is shown in FIG. 16. The enzyme was stored in a heavy duty liquid detergents adjusted to various pH at 40° C. for one month and, then, residual activity of the enzyme was measured using keratin as a substrate. pH was adjusted with glycine-NaOH buffer or sulfonic acid. Meanwhile, the enzyme was stored in a heavy duty liquid detergent (pH 11) at various temperatures for one month. As seen from FIG. 16, when enzyme Ya was stored in the heavy duty liquid detergent at 40° C. for one month, the fully activity remained at pH 9.0 and half the activity remained at pH 10.0. Regarding temperature dependency, upon storage at pH 11 for one month, the full activity remained at temperatures below 25° C. and 65% remained at a temperature of 35° C. Thus, enzyme Ya has excellent stability in heavy duty liquid detergents, compared with known alkaline protease.

Figure 17:
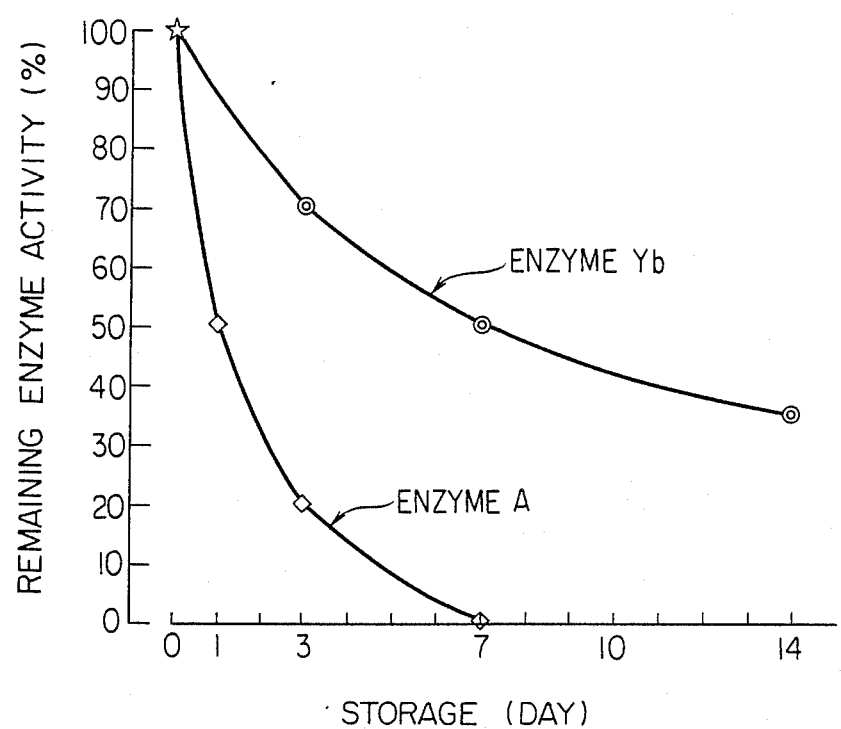

Stability of enzyme Yb during storage in a heavy duty liquid detergent is shown in FIG. 17. The enzyme was stored at 40° C. in a heavy duty liquid detergent, the pH of which was adjusted to 11 with a glycine-NaOH buffer solution. Residual activity of the enzyme for decomposition of keratin was measured by day.

The results are shown in FIG. 17. Enzyme A was inactivated by 80% on the third day and inactivated completely on the seventh day. On the other hand, 70% of the activity of enzyme Yb remained on the third day and 50% remained on the seventh day. Thus, enzyme Yb has excellent stability in high pH heavy duty liquid detergents, compared to known alkaline protease.

The test for enzyme stability in a heavy duty liquid detergent was carried out in an accelerated test condition at a higher temperature than room temperature, and therefore the results show that enzyme Ya and enzyme Yb of this invention are stable under normal condition from the practical point of view.

(viii) Molecular weight

Figure 18:
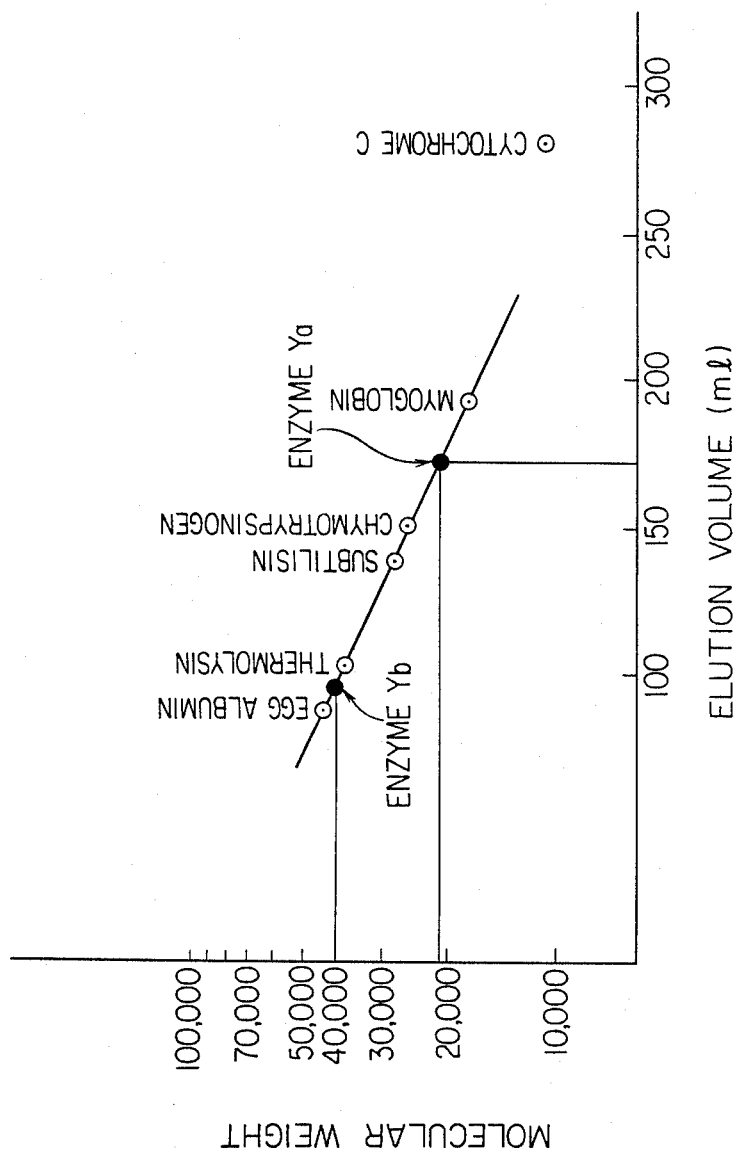
FIG. 18 is a graph which shows a calibration curve for determination of molecular weights of enzyme Ya and enzyme Yb.

Molecular weights of enzyme Ya and enzyme Yb were determined by gel filtration method. Gel filtration chromatography was carried out on a Toyopearl HW-55 (trademark) using 20 mM Tris-HCl buffer (2 mM $Ca^{2+}$ ion added, pH 7.2), as eluent. The following proteins (molecular weight in parenthese) were used as standard proteins to draw a calibration curve: egg albumin (43,000), thermolysin (37,500), subtilisin (27,300), chymotrypsinogen (25,700), myoglobin (17,200) and cytochrome C (11,700). The calibration curve is shown in FIG. 18. In this method, molecular weights of enzyme Ya and enzyme Yb were determined as 21,000 and 40,000, respectively.

(ix) Isoelectric point

Figure 19:
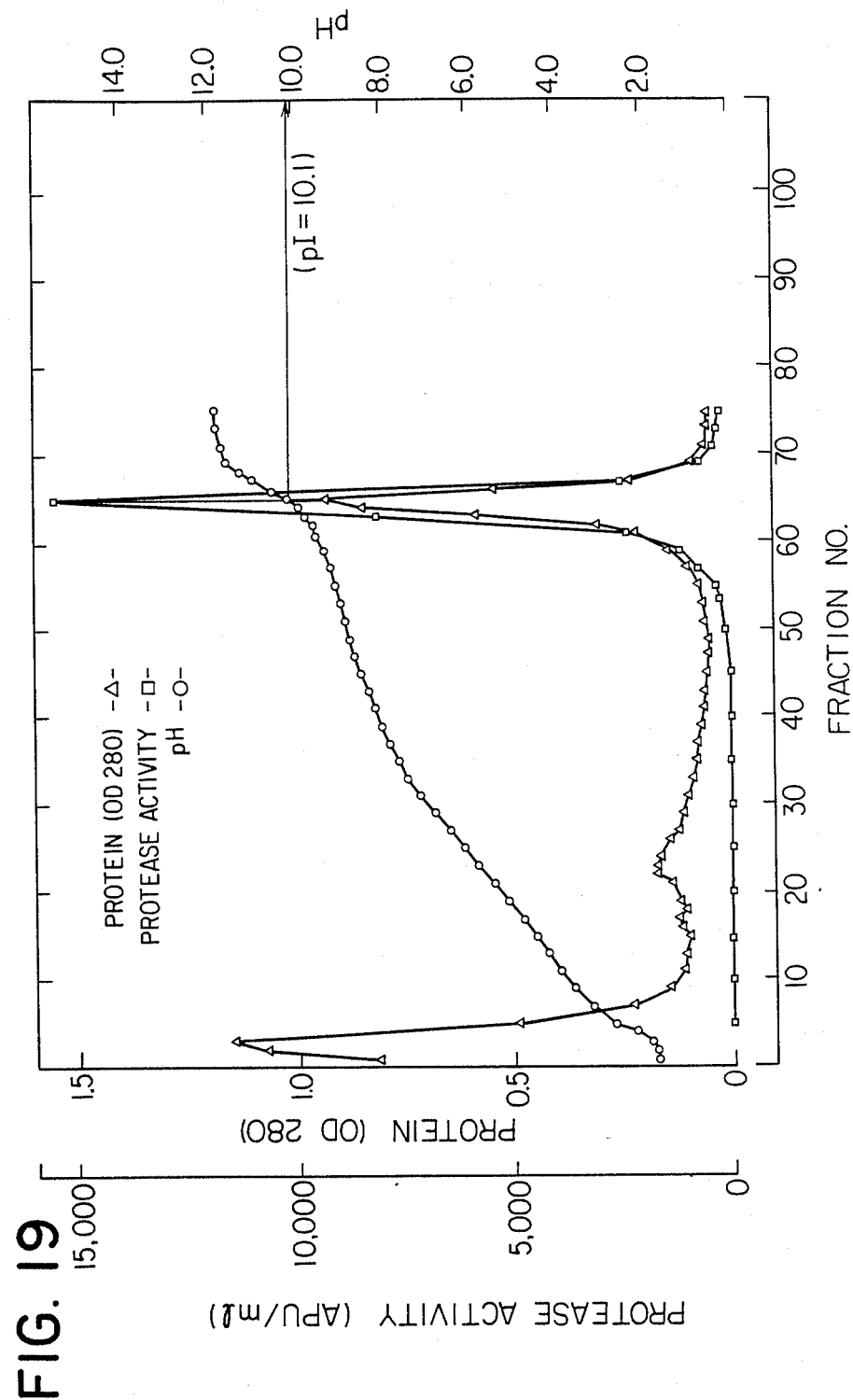
FIGS. 19 and 20 are graphs which show patterns of an isoelectric focusing electrophoresis of enzyme Ya and enzyme Yb, respectively.
Figure 20:
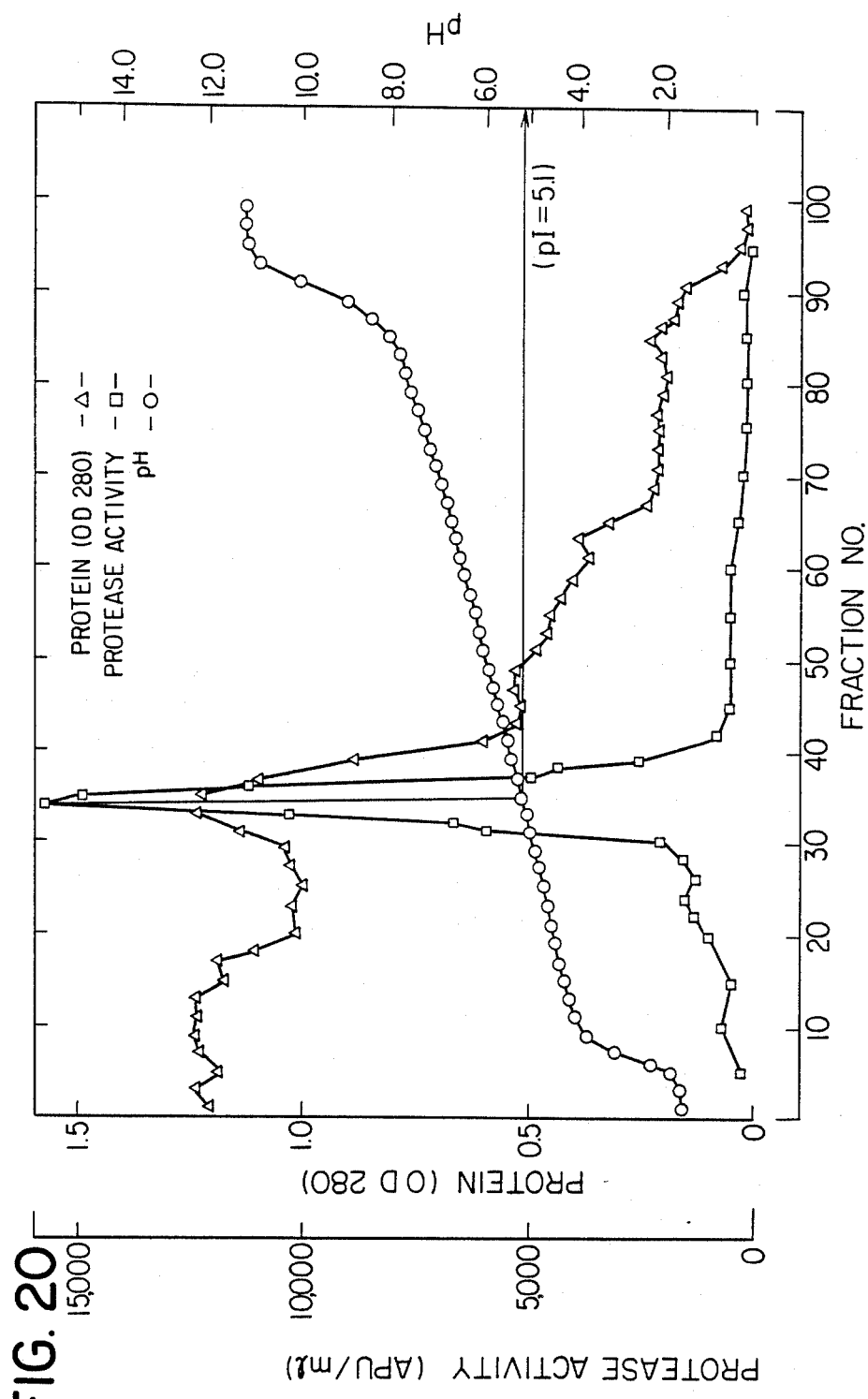

Isoelectric points of enzyme Ya and enzyme Yb were determined by isoelectric focusing electrophoresis. Pharmalyte 3-10 was used as a column carrier. Patterns of isoelectric focusing electrophoresis for enzyme Ya and enzyme Yb are shown in FIGS. 19 and 20, respectively. The isoelectric points of enzyme Ya and enzyme Yb were determined by this method as 10.1 and 5.1, respectively.

and other known alkaline proteases produced by alkalophilic bacteria belonging to the genus Bacillus.

TABLE 9

|  | Enzyme Ya | Enzyme Yb | Enzyme A[a] | No. 221[b] | E-1[c] | E-2 (C) | API-21[d] |
|---|---|---|---|---|---|---|---|
| Producing Bacterium | Bacillus sp Y Strain | | Bacillus licheniformis | Alkalophilic Bacillus Species | | | |
|  |  |  |  | Bacillus | Bacillus No. D-6 | | Bacillus NKS-21 |
| Optimal pH | 10–12.5 | 9–10 | 10–11 | 11–12 | 10–11 | 10–11 | 10–11 |
| Optimal Temperature | 70° | 65–70° C. | 60° C. | 60° C. | 75° C. | 75° C. | 45–50° C. |
| Thermal Stability |  |  |  |  |  |  |  |
| None | 55° C. | 50° C. | 40° C. | 50° C. | 55° C. | 55° C. | 40° C. |
| 5 m M $Ca^{2+}$ | 60° C. | 60° C. | 50° C. | 60° C. | Improvement on thermal stability by $Ca^{2+}$ ion is not recognized. | | — |
| Molecular Weight | 21,000 | 40,000 | 27,300 | 30,000 | 20,000 | 20,000 | 22,000 |
| Isoelectric Point | 10.1 | 5.1 | 9.4 | 9.4 | 10.0 | 6.5 | 7.4 |

[a] E. L. Smith, et al. J. Biol. Chem., 243, 2181, (1968)
[b] K. Horikoshi, Agr. Biol. Chem., Vol. 35, No. 9, 1407 (1971)
[c] K. Horikoshi, Japanese Patent Publication (examined) 4236/1981
[d] E. Ichishima, Japanese Patent Publication (unexamined) 134990/1983

(x) Amino acid composition

Amino acid compositions of enzyme Ya and enzyme Yb were determined using an amino acid analyzer JLC-200A (Japan Electronic Co.). Tryptophan and cystein were determined by a spectrophotometric method and a performic acid oxidation method, respectively. The compositions are shown in Table 7 in comparison with the compositions of known proteases.

Enzyme Ya clearly differs from other enzymes in amino acids such as tryptophan, serine and valine. Enzyme Yb shows clear difference from other enzymes in amino acids such as tryptophan, histidine, arginine, aspartic acid, glycine and alanine.

TABLE 7

| | Enzyme | | | | |
|---|---|---|---|---|---|
| Amine Acid | Enzyme Ya | Enzyme Yb | Enzyme A (a) | Subtilisin BPN (b) | Subtilisin NOVO (c) |
| Tryptophan | 5 | 11 | 1 | 3 | 3 |
| Lysine | 7 | 6 | 9 | 11 | 6 |
| Histidine | 5 | 13 | 5 | 6 | 5 |
| Arginine | 5 | 10 | 4 | 2 | 3 |
| Aspartic acid | 20 | 53 | 28 | 28 | 20 |
| Threonine | 11 | 18 | 19 | 13 | 14 |
| Serine | 22 | 32 | 32 | 37 | 37 |
| Glutamic acid | 9 | 17 | 12 | 15 | 12 |
| Proline | 9 | 14 | 9 | 14 | 10 |
| Glycine | 22 | 46 | 35 | 33 | 25 |
| Alanine | 20 | 50 | 41 | 37 | 27 |
| Valine | 9 | 35 | 31 | 30 | 20 |
| Methionine | 2 | 4 | 5 | 5 | 3 |
| Isoleucine | 6 | 15 | 10 | 13 | 12 |
| Leucine | 10 | 21 | 16 | 15 | 12 |
| Tyrosine | 6 | 14 | 13 | 10 | 9 |
| Phenylalanine | 4 | 4 | 4 | 3 | 2 |
| Cystein | 0 | 0 | 0 | 0 | 0 |

(a) E. L. Smith, J. Biol. Chem., 243, 2181. (1968).
(b) F. S. Merkaland, J. Biol. Chem., 242, 5198 (1967).
(c) D. Turu, Agr. Biol. Chem., 31, 330 (1967).

(xi) Elemental analysis

Results of elemental analysis of enzyme Ya and Yb are shown in Table 8.

TABLE 8

|  | Enzyme Ya | Enzyme Yb |
|---|---|---|
| C | 44.82% | 52.55% |
| H | 7.27% | 6.54% |
| N | 13.96% | 13.81% |
| S | 0.33% | 0.34% |

Various properties of enzyme Ya and enzyme Yb are summarized in Table 9 in comparison with Enzyme A Comparing enzyme Ya and enzyme Yb according to the invention with known alkaline proteases, the optimal pH is 10 to 11 for enzyme A, E-1, E-2 and API-21 and 11 to 12 for No. 221, while it is 10 to 12.5 for enzyme Ya, that is, it extends to a higher pH range. The optimal pH for enzyme Yb is 9 to 10 which is lower than those for enzyme Ya and other known alkaline proteases.

The optimal temperature of enzyme ya and enzyme Yb is around 70° C.. However, the optimal temperature is as low as 60° C. for enzyme A and No. 221, and 45 to 50° C. for API-21. That for E-1 and E-2 is 75° C., which is higher than that of the present enzymes. The present enzymes differ from other known enzymes also in this point.

The thermal stability of the present enzymes as well as enzyme A, No. 221 and API-21 is increased by about 5 to 10° C. in the presence of 5 mM $Ca^{2+}$ ion. However, the thermal stability of E-1 and E-2 produced by Bacillus No. D-6 strain (see, the footnote of Table 9) are not increased.

Further, the molecular weight of enzyme Yb is 40,000 which is higher than those of known alkaline proteases, and its isoelectric point is as low as pI 5.1. Accordingly, Yb is clearly of a different enzyme.

Judging from the above, the present enzymes differ from any of known alkaline proteases. Therefore, it is quite reasonable to recognize enzyme Ya and enzyme Yb as being novel, so that they are designated alkaline proteases Ya and Yb, respectively.

DETERGENT COMPOSITIONS

The novel alkaline proteases of this invention can be blended in a heavy duty liquid detergent or heavy duty detergent. Particularly, when blended in a highly alkaline detergent for clothes, the alkaline proteases of this invention give remarkable results as compared with alkaline proteases of the prior art.

Suitable formulations of heavy duty liquid detergents containing the protease of this invention are as follows:

|  | Formulation (wt. %) | Preferred formulation (wt. %) |
|---|---|---|
| Surfactant | 10–50 | 20–40 |
| Solubilizer | 0–10 | 2–8 |

|  | Formulation (wt. %) | Preferred formulation (wt. %) |
| --- | --- | --- |
| Ethanol or Isopropanol | 0–20 | 3–10 |
| Alkali component | 0–20 | 0.5–10 |
| Minor component | 0–3 | 0.1–2 |
| Alkaline protease | 100–100,000 APU/g | 1,000–2,000 APU/g |
| Water | balance | balance |

The heavy duty liquid detergents can be prepared by blending the above components in any manner. The pH of the heavy duty liquid detergents is 7 to 11, preferably 10 to 11.

Suitable formulations of granular detergents containing the protease of this invention are as follows:

|  | Formulation(wt. %) |
| --- | --- |
| Surfactant | 10–50 |
| A-type zeolite | 10–30 |
| Sodium silicate (SiO$_2$/Na$_2$O = 2–3/1) | 5–20 |
| Sodium sulfate | 1–30 |
| Minor component | 0–5 |
| Alkaline protease | 100–100,000 APU/g |
| Water | 3–15 |

In the detergents of this invention, there can be used any of anionic, nonionic and amphoteric surfactants. Anionic surfactants include sodium $C_{10}$–$C_{15}$ alkylethoxysulfates, $C_{12}$–$C_{18}$ alpha-olefin sulfonates, $C_{11}$–$C_{16}$ alkylsulfates, $C_{10}$–$C_{13}$ alkyl benzene sulfonates, nonionic surfactants include $C_{10}$–$C_{15}$ alkyl ethoxylates, $C_{10}$–$C_{13}$ alkylphenyl ethoxylates, $C_{10}$–$C_{16}$ alkylamine ethylene oxide addition products, and ampholytic surfactants include $C_{11}$–$C_{15}$ alkylbetaines.

EXAMPLE

This invention will now be explained in detail with reference to the following non-limitative examples.

EXAMPLE 1

The screening procedure which the present inventors used for isolating the present strains from the natural field will be explained below in detail.

(1) Isolation of alkalophilic bacteria

About 100 mg of soil from one of various places was incubated in a test tube (16.5 mm in diameter × 165 mm) which contained 5 ml of a liquid medium (pH 11) including 0.5% yeast extract, 0.05% polypeptone, 0.1% dipotassium hydrogen phosphate, 0.02% magnesium sulfate and 1% sodium carbonate and transferred at 37° C. for 5 days. The culture liquid was inoculated to a plate containing the above medium and 1.5% agar and incubated at 37° C. for 3 days to obtain alkalophilic bacteria.

(2) Isolation of alkaline protease-producing bacteria

The alkalophilic bacteria obtained in the procedure (1) above were stabbed onto a skim milk medium plate (pH 10) containing 1% skim milk, 0.025% yeast extract, 0.05% peptone, 1% sodium carbonate and 1.5% agar, and incubated at 37° C. for 24 hours. Then, ones which formed halo were collected as alkaline protease-producing bacteria.

(3) Isolation of alkaline protease-producing bacteria having resistance to surfactants The culture fluid obtained in the conditions of medium and incubation as described in the procedure (1) above was centrifuged at 8000 rpm for 5 minutes to obtain a culture supernatant. 20 μl each of the supernatent per se and the supernatant admixed with a detergent at 300 ppm and incubated at 40° C. for one hour were placed on paper discs used for detection of anitbiotics (8 mm in diameter) and, further, put on a skim milk medium (pH 10) as described above. Both were incubated at 37° C. for 24 hours and the diameters of halos were measured. Those whose halo diameter was the same both in the case of detergent treatment and in the case of no treatment were collected as alkaline protease-producing bacteria resistant to surfactants.

(4) Selection of the bacteria producing alkaline proteases which are stable in highly alkaline detergents and contribute to improvement of detergency Enzymes were prepared by cultivation of bacteria at 30° C. for 3 days in liquid media containing 2% soluble starch, 0.5% yeast extract, 0.5% polypeptone, 0.1% dipotassium hydrogen phosphate, 0.02% magnesium sulfate and 1% sodium carbonate, followed by centrifugation, salting-out with 70% ammonium sulfate and dialysis. For a test of stability in high pH heavy duty detergent (pH 11), 6.6 g glycine and 3.3 g NaOH were added to 100 g of a heavy duty liquid detergent commercially available and, further, about 10 ml of the above enzyme solution (300,000 APU on a casein substrate) were added, which was stored at 40° C. for one week and evaluated for the remaining activity. Ones which maintained 50% or more of the activity were selected.

Washing tests were conducted according to the method described in Yu-kagaku (Oil Chemistry), 30, 432 (1981). Clothes to be washed were stained with artificial wet-stains blended with protein. For evaluation, each of the enzymes (5,000 APU) was blended with a detergent (1 g), and a detergent with no enzyme was used as a standard. Ones which had higher washing ability than the standard by 4% or more (such improvement of washing ability can be easily recognized with the naked eye) were selected. The number of bacteria which were selected through the above screening steps are shown in table 10.

TABLE 10

| Collected soils | 330 places in Japan |
| --- | --- |
| (1) Isolated alkalophilic bacteria | 681 strains |
| (2) Alkaline protease-producing bacteria | 241 strains |
| (3) Surfactant resistant alkaline protease-producing bacteria | 23 strains |
| (4) Bacteria producing alkaline protease which is stable in highly alkaline detergents and contribute to improvement of detergency | 4 strains (Y, P, K and X) |

The bacteria selected by the above screening from the natural field are novel Bacillus sp. Y (FERM BP-1029), P (FERM BP-1030), K (FERM BP-1031) and X (FERM BP-1032) according to the invention, which belong to the genus Bacillus and have ability to produce alkaline proteases which have excellent stability in highly alkaline detergents and contribute to improvement of detergency.

The places where these bacteria were collected are Chiba, Japan, for strain Y, an agricultural field in Sakahogi, Gifu, Japan, for strain P, Ito, Shizuoka, Japan, for strain K, and an agricultural field in Tama, Tokyo, Japan, for strain X. Collections were carried out in 1982 to 1983.

Figure 3:
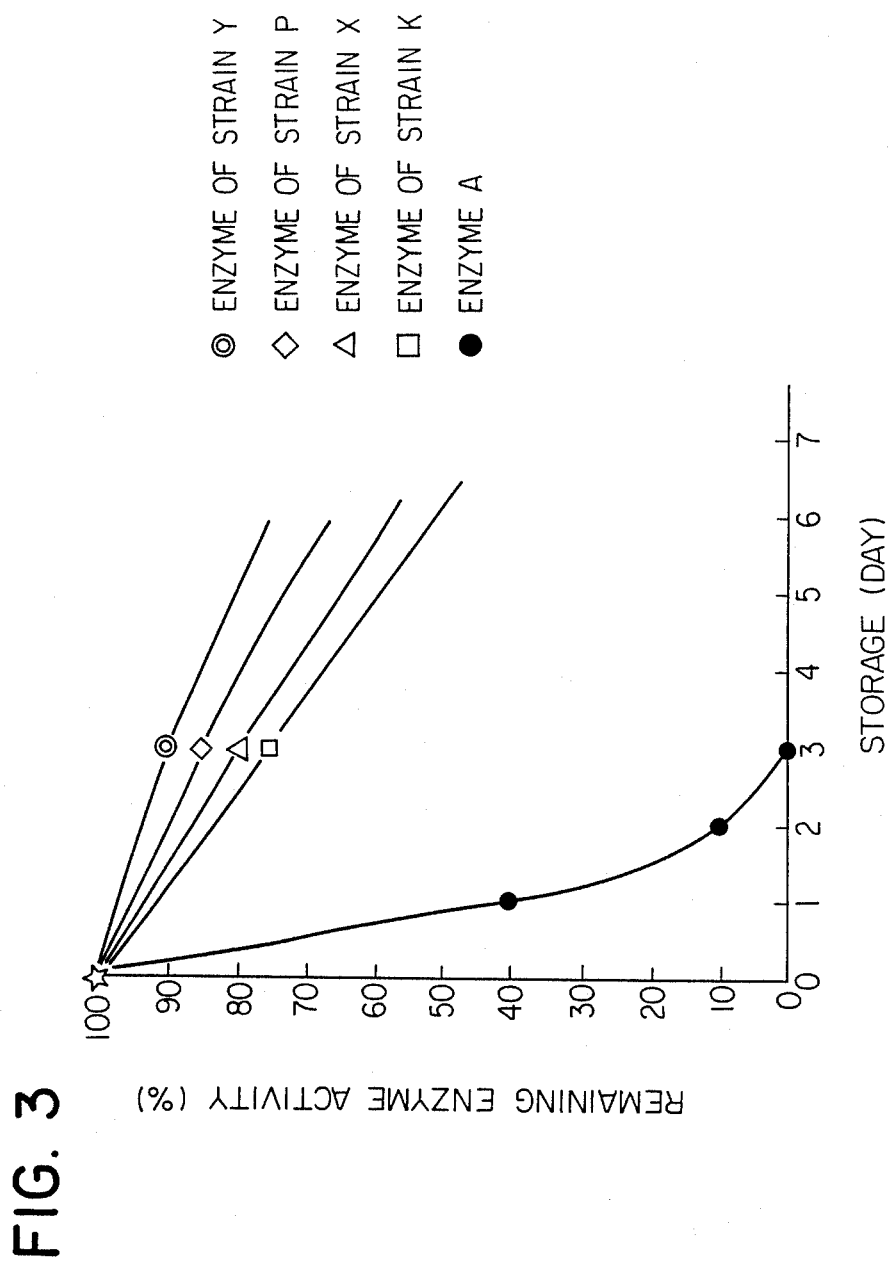
FIG. 3 is a graph which shows stability of alkaline proteases produced by the present bacterial strains, in a high pH detergent solution (pH 11).

Stability of the alkaline proteases produced by strains Y, P, K and X in a heavy duty liquid detergent (pH 11) is shown in FIG. 3.

Further, the above proteases produced by those bacteria were blended with a detergent and the degree of improvement of detergency was examined. The results are shown in Table 11. Washing tests were carried out according to the method described in Yu-kagaku (Oil Chemistry), 30, 432 (1981). Cloths to be washed were stained with artificial stains blended with protein.

TABLE 11

| Sample | Detergency (%) |
|---|---|
| No Enzyme Added | 74 |
| Enzyme from Strain Y | 79 |
| Enzyme from Strain P | 78 |
| Enzyme from Strain K | 78 |
| Enzyme from Strain X | 79 |

These results show that the strains according to the invention have an advantage that they produce alkaline proteases which have excellent stability in highly alkaline conditions in the co-existence of detergent constituents and which contribute to improvement of detergency.

EXAMPLE 2

CULTURE OF STRAINS

A liquid medium containing 2% soluble starch and 0.02% magnesium sulfate and a liquid medium containing 1% dried yeast and 0.1% dipotassium hydrogen phosphate were separately sterilized at 121° C. for 20 minutes and 20 ml of each was poured into a 500 ml Sakaguchi flask and, further, sterilized sodium carbonate was added to a final concentration of 1% to prepare a 50 ml culture broth. Bacillus sp. Y strain was inoculated to the culture broth and incubated at 30° C. for 15 hours to prepare a seed culture. 100 ml of the seed culture was inoculated to a 7l-fermentor containing 3.5 l of the medium having the same composition, which was then cultivated with aeration (1 vvm) and stirring (500 rpm) at 30° C. for 70 hours. The resultant culture fluid of 3.5 l (2,500 APU/ml) was centrifuged at 10,000 rpm for 5 minutes to remove the bacteria. An approximately 3.0 l surpernatant was obtained.

Purification of enzyme Ya

To 2650 ml of the supernatant thus obtained, 1250 g ammonium sulfate was added while cooling and stirring the supernatant. The precipitates were collected by centrifugation and were dissolved in 500 ml of 20 mM Tris-HCl buffer (pH 7.2, containing 2 mM $Ca^{2+}$ ion). The solution was placed in a dialysis tube and dialysed against the same buffer overnight. Thus, crude enzyme solution A (890 ml, 6600 APU/ml, specific activity 4350 APU/mg protein) was obtained. The above solution was applied on to a DEAE-53 cellulose column (3.2φ×40 cm) equilibrated with 20 mM Tris-HCl buffer (pH 7.2) and eluted with the same buffer. Unabsorbed active fractions were collected, which amounted to 420 ml: activity, 11,300 APU/ml; specific activity, 11,800 APU/mg protein. After the procedure up to here, the specific activity had increased about 6.2-hold with a 72% recovery. Further, 198 g of ammonium sulfate were added to the above fractions to salt out proteins. Then, the precipitates were dissolved in 300 ml of 20 mM Tris-HCl buffer (pH 7.2, containing 2 mM $Ca^{2+}$ ion). The solution was subjected to gel filtration using Toyopearl HW-55 (trademark) and eluted with the same buffer. The resultant active fractions were subjected to ammonium sulfate precipitation and precipitates were dissolved in 10 ml of the same buffer solution followed by dialysis. After dialysis, insoluble material was removerd with a Millex filter (trademark) to obtain a 16.4 ml solution: activity 210,000 APU/ml; specific activity 15,900 APU/mg protein. This purification procedures are summarized in Table 12.

PURIFICATION OF ENZYME Yb

The aforesaid crude enzyme solution A was applied on to a DEAE-53 cellulose column equilibrated with 20 mM Tris-HCl buffer (2 mM $Ca^{2+}$ ion added, pH 7.2) and enzyme Ya was eluted with the same buffer. Then, enzyme Yb was eluted with the linear gradient of 0 to 0.5 M sodium chloride in the same buffer, and active fractions were collected, which amounted to 350 ml: activity 4,200 APU/ml; specific activity 1350 APU/mg protein.

Then, these active fractions of Yb were subjected to hemoglobin-agarose affinity column chromatography and eluted with 50 mM sodium phosphate buffer (pH 7.0) to collect active fractions. Recovery rate was 15% and specific activity was 7400 APU/mg protein.

Further, the above solution was subjected to gel filtration on Toyopearl HW-55 (trademark) and eluted with 20 mM Tris-HCl buffer (2 mM $Ca^{2+}$ ion added, pH 7.2). The resultant active fractions were subjected to salting-out with ammonium sulfate and the precipitates were dissolved in 3 ml of the same buffer and dialysed against the same one.

After dialysis, a solution of 7 ml was obtained: activity 94,000 APU/ml; specific activity 8,500 APU/mg protein. The purification procedures are summarized in Table 13.

TABLE 12

| | Enzyme Ya | | | | | |
|---|---|---|---|---|---|---|
| Steps | Volume (ml) | Activity (APU/ml) | Protein (mg/ml) | Overall Activity (APU) | Specific Activity (APU/mg protein) | Yield (%) |
| Supernatant of Culture Fluid | 2650 | 2500 | 1.3 | 6600000 | 1900 | 100 |
| Ammonium Sulfate Fractionation | 890 | 6600 | 1.5 | 5900000 | 4350 | 90 |
| Anion Exchange Chromatography | 420 | 11300 | 0.96 | 4750000 | 11800 | 72 |
| Gel Filtration | 130 | 29000 | 2.1 | 3770000 | 13800 | 57 |
| Condensation (($NH_4$)$SO_4$) | 16.4 | 210000 | 13.2 | 3440000 | 15900 | 52 |

TABLE 13

Enzyme Yb

| Steps | Volume (ml) | Activity (APU/ml) | Protein (mg/ml) | Overall Activity (APU) | Specific Activity (APU/mg protein) | Yield (%) |
|---|---|---|---|---|---|---|
| Supernatant of Culture Fluid | 2650 | 2500 | 1.3 | 6600000 | 1900 | 100 |
| Ammonium Sulfate Fractionation | 890 | 6600 | 1.5 | 5900000 | 4350 | 90 |
| Anion Exchange Chromatography | 350 | 4200 | 3.1 | 1470000 | 1350 | 22 |
| Affinity Chromatography | 190 | 5200 | 0.7 | 990000 | 7400 | 15 |
| Gel Filtration | 46 | 17000 | 2.0 | 780000 | 8500 | 12 |
| Condensation ((NH$_4$)SO$_4$) | 7 | 94000 | 11.0 | 660000 | 8500 | 10 |

Figure 21:
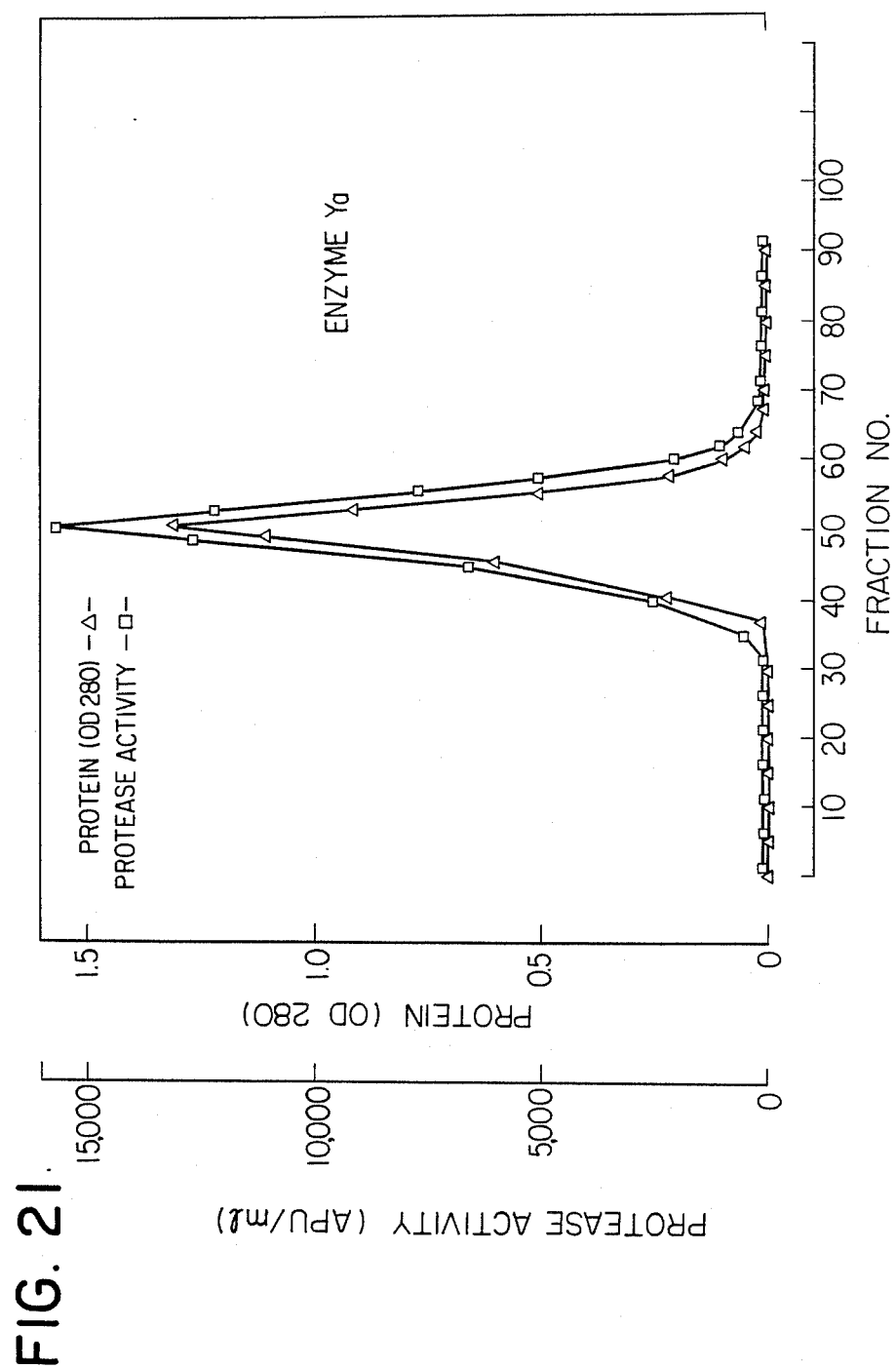
FIGS. 21 and 22 are graphs which show elution patterns of enzyme Ya and enzyme Yb, respectively, in gel filtration.
Figure 22:
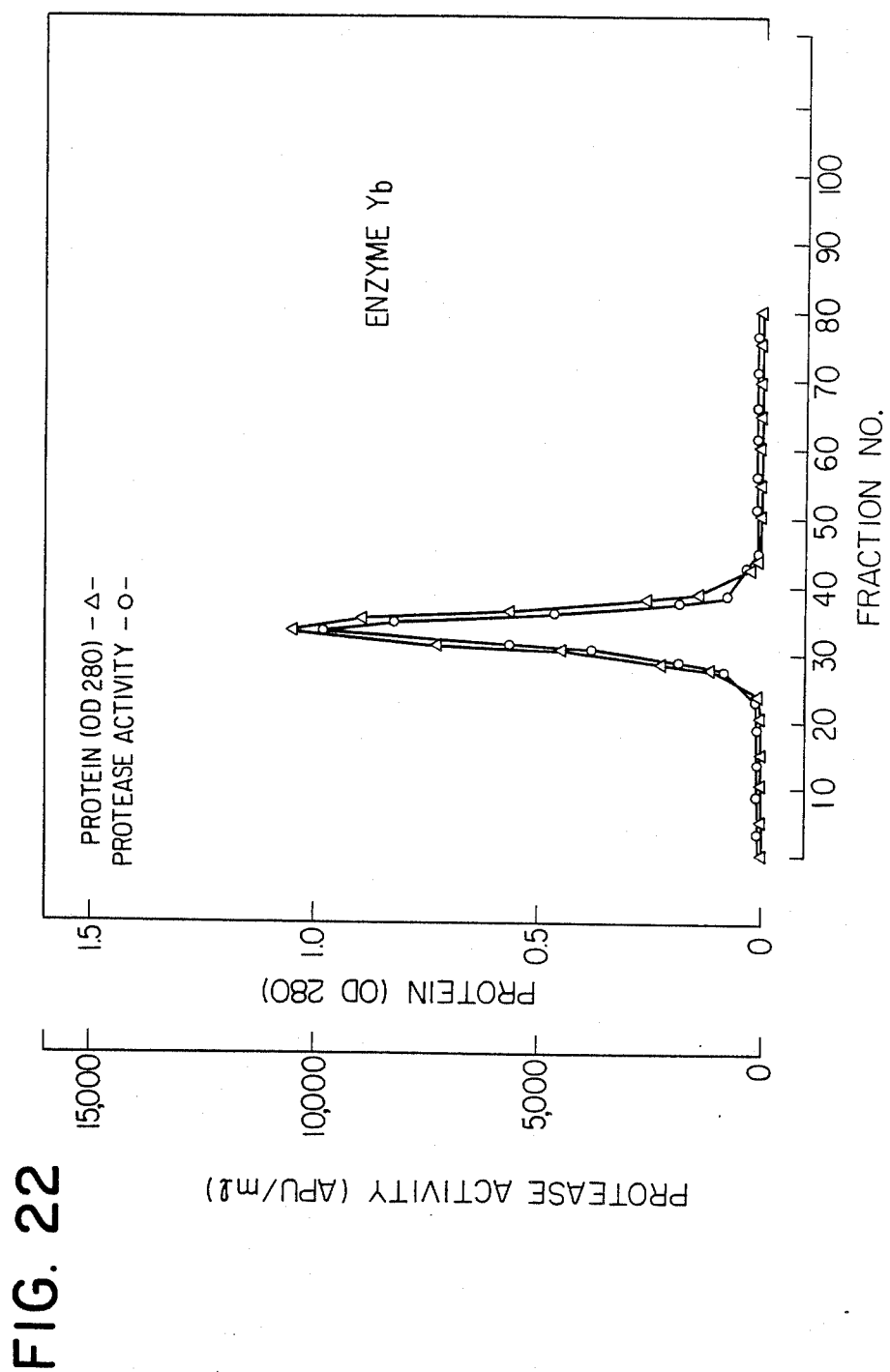

FIGS. 21 and 22 show elution patterns of enzyme Ya and enzyme Yb in gel filtration (Toyopearl HW-55), respectively. The eluting solution was 20 mM Tris-HCl buffer (pH 7.2, containing 2 mM Ca$^{2+}$ ion).

As seen from the above figures, enzyme Ya and enzyme Yb were completely purified by the aforesaid purification procedures.

Figure 23:
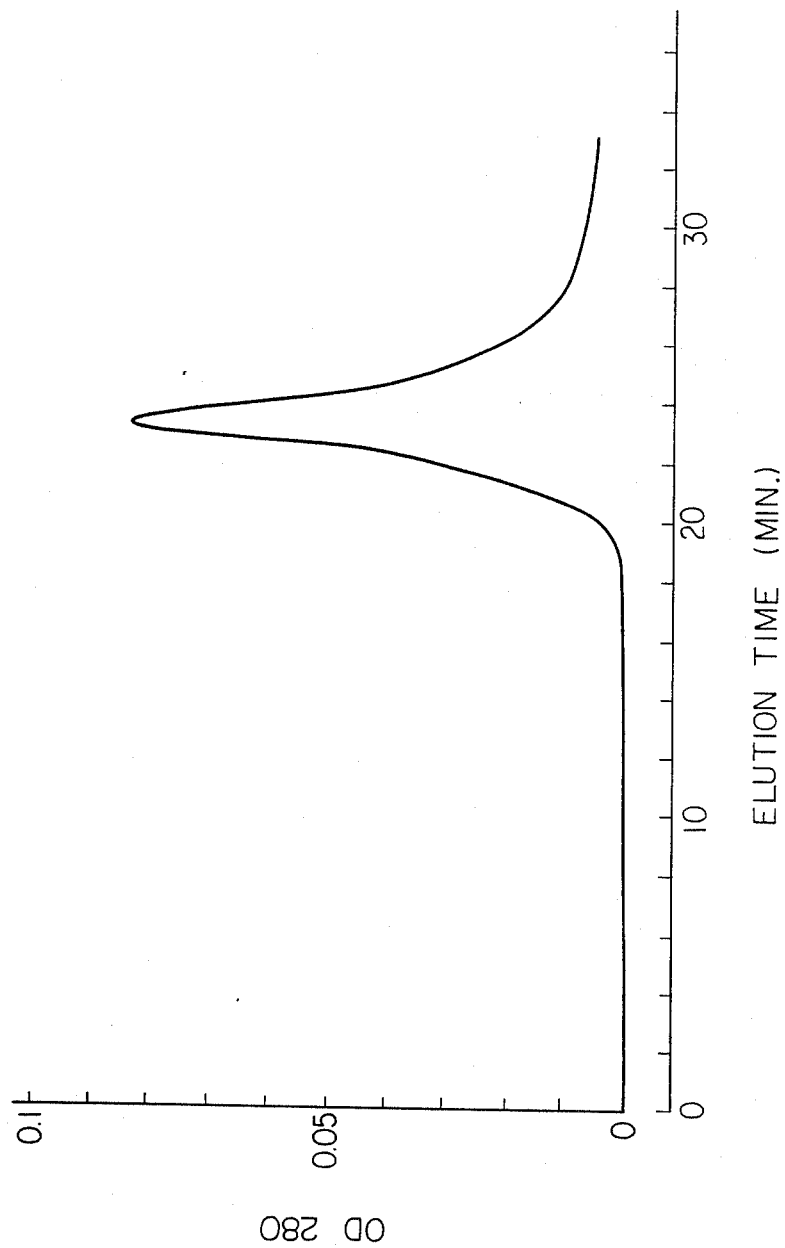
FIG. 23 is a graph which shows an elution pattern of enzyme Ya in high performance liquid chromatography.

FIG. 23 shows an elution pattern of purified enzyme Ya in high performance liquid chromatography (Waters W1SP-710B, two I-125 columns in series). An eluant was 50 mM Sodium phosphate buffer (pH 7.0).

DETERGENCY OF THE PRESENT ENZYMES

A blend of 20 wt. % sodium C$_{13}$ alkyl (straight chain ratio: 50%) polyethoxy sulfate (average addition mole number of ethylene oxide: (3), 10 wt. % C$_{13}$ alkyl (straight chain ratio: 50%) alcohol ethoxylate (average addition mole number of ethylene oxide: (15), 6 wt. % ethanol, 6 wt. % sodium toluenesulfonate, alkaline builder (6.6 wt. % glycine, 3.3 wt. % NaOH) and water to balance was prepared as a standard composition of a detergent. The pH of this detergent was 11. An enzyme was blended with the above detergent in an amount of 5,000 APU/g (casein as a substrate). A sample composed only of the above composition without an enzyme was designated as Sample-1. Samples composed of the above composition and enzyme Ya or Yb were designated as Sample-2 and Sample-3, respectively.

Further, crude enzyme (specific activity, 4350 APU/mg protein) prepared according to the above purification method (containing Ya and Yb at a ratio of 2:1) was added to the above composition, which was designated as Sample-4. For comparison, enzyme A or Esperase (trademark, Novo Industri A/S) was blended with the above composition to prepare Samples 5 and 6, respectively. For evaluating the inactivation of enzymes after long period of storage, detergency was determined for samples not only immediately after blending but also after storage at 40° C. for 7 days.

Terg-O-Tometer (US-Testing Co.) was used as a washing machine. 10 cloths stained with wet stain blended with protein, 3 Sebum cloths and cleaned knitted cloth (amounted to 30 g) were put into 0.1% detergent solution (900 ml) and the cloths were washed at 120 rpm, 25° C. for 10 minutes. Rinsing was carried out with 900 ml water for 3 minutes. The used water had a hardness of 3° DH. An index of detergency was calculated based on the following equation described in Yukagaku (Oil Chemistry), 30, 432 (1981). The results are shown in Table 14.

Detergency (%) =

$$\frac{K/S \text{ of stained cloth} - K/S \text{ of washed cloth}}{K/S \text{ of stained cloth} - K/S \text{ of unstained cloth}} \times 100$$

wherein, $$K/S = \left(1 - \frac{R}{100}\right)^2 / \frac{2R}{100}$$

K: light absorbance coefficient of cloth
S: light scattering coefficient of cloth
R: reflectance (%)

TABLE 14

| Sample No. | Enzyme | Detergency (%) Immediately after formulation | After storage at 40° C. for 7 days |
|---|---|---|---|
| 1 | — | 74 | 74 |
| 2 | enzyme Ya | 79 | 79 |
| 3 | enzyme Yb | 78 | 78 |
| 4 | crude enzyme Y | 80 | 80 |
| 5 | enzyme A | 78 | 74 |
| 6 | Esperase | 75 | 75 |

As seen from the above results, the samples containing the enzymes of this invention had significantly higher detergency than the samples containing no enzyme both immediately after formulation and after storage at 40° C. for 7 days and the enzymes of this invention contributed to improving detergency of heavy duty liquid detergents.

Sample-4 which contained the crude enzymes of this invention had slightly better detergency. Accordingly, combinational use of Ya and Yb, which have different substrate specificities, is desirable from the view points of performance and economy, though the present enzymes can be used alone.

It is naturally expected that combinational use of Ya, Yb and known enzymes will further improve detergency effectively, because enzymes Ya and Yb have various physicochemical properties different from those of known enzymes. The enzymes can also be used for a heavy duty detergent alone or in combination with one or more of other known enzymes.

The enzymes of this invention were blended with other detergent compositions to evaluate the degree of improvement of detergency given by the enzymes. As an alkaline builder, 6.6 wt. % glycine and 3.3 wt. % NaOH were added. The crude enzyme was used in an amount of 5,000 APU per g of the detergent compositions. Detergency of the compositions was determined after they were stored at 40° C. for 7 days. The results are shown in Table 15.

TABLE 15

|  | Sample No. 1 | Sample No. 2 |
|---|---|---|
| AES-Na (1) | 20 wt. % |  |
| AES-Na (2) |  | 15 wt. % |
| AE (1) | 15 wt. % |  |
| AE (2) |  | 20 wt. % |
| TS-Na | 5 wt. % |  |
| Ethanol | 5 wt. % | 10 wt. % |
| Water | balance | balance |
| Washing ability (%) | 80 | 80 |

AES-Na (1): Sodium $C_{13}$ alkyl (straight chain ratio: 50%) polyethoxy sulfate (average addition mole number of ethylene oxide: 3)
AES-Na (2): Sodium $C_{12-13}$ alkyl (straight chain ratio: 80%) polyethoxy sulfate (average addition mole number of ethylene oxide: 5)
AE (1): $C_{13}$ alkyl (straight chain ratio: 50%) alcohol ethoxylate (average addition mole number of ethylene oxide: 9)
AE (2): $C_{12-13}$ alkyl (straight chain ratio: 80%) alcohol ethoxylate (average addition mole number of ethylene oxide: 20)

Table 15 demonstrates that the enzymes of this invention improve the detergency of these detergent compositions.

What we claim is:

1. Alkaline protease Ya having the following physicochemical properties:
   a. activity: decomposes various proteins in highly alkaline conditions,
   b. substrate specificity: remarkably specific to insoluble proteins, particularly to keratin,
   c. optimal pH: pH 10.0 to 12.5 when reacted at 35° C. for 10 minutes on a casein substrate,
   d. pH range for stability: pH 6.5 to 13.0 when incubated at 25° C. for 24 hours on a casein substrate,
   e. optimal temperature: 70° C. when reacted at pH 10.5 on a casein substrate,
   f. thermal stability: at least 90% of the activity remains after incubation at pH 10.5 and 60° C. for 10 minutes,
   g. absorption spectrum: maximum absorption at 276 nm in 50 mM Tris-HCl buffer of pH 8.0,
   h. effect of metal ions: the activity is inhibited by $Hg^{2+}$ ion and thermal stability of the enzyme is increased by $Ca^{2+}$ ion when casein is used as a substrate,
   i. effect of inhibitors: when casein used as a substrate, the activity is not inhibited by EDTA (ethylenediaminetetraacetate) and PCMB (p-chloromercury benzoate), but inhibited by DFP (diisopropylfluorophosphate) and PMSF (phenylmethylsulfonyl fluoride),
   j. effect of surfactants: when stored in heavy duty liquid detergent at 40° C. for one month, the full activity remains at pH 9.0 and 50% of the activity at pH 10.5,
   k. molecular weight: 21,000 (gel filtration method using Toyopearl HW-55), and
   l. isoelectric point: 10.1 (isoelectric focusing electrophoresis method using Pharmalyte 3-10).

2. Alkaline protease Yb having the following physicochemical properties:
   a. activity: decomposes various proteins in highly alkaline conditions,
   b. substrate specificity: remarkably specific to egg albumen,
   c. optimal pH: pH 9.0 to 10.0 when reacted at 35° C. for 10 minutes on a casein substrate,
   d. pH range for stability: pH 6.5 to 12.0 when treated at 25° C. for 24 hours on a casein substrate,
   e. optimal temperature: 65° to 70° C. when reacted at pH 10.5 on a casein substrate,
   f. thermal stability: at least 90% of the activity remains after incubation at pH 10.5 and 60° C. for 10 minutes,
   g. absorption spectrum: maximum absorption at 278 in a 50 mM Tris-HCl buffer solution of pH 8.0,
   h. influence of metal ions: the activity is inhibited by $Hg^{2+}$ ion and thermal stability of the enzyme is increased by $Ca^{2+}$ ion when casein used as a substrate,
   i. effect of inhibitors: when casein is used as a substrate, the activity is not inhibited by EDTA (ethylenediaminetetraacetate) and PCMB (p-chloromercury benzoate), but inhibited by DFP (diisopropylfluorophosphate) and PMSF (phenylmethylsulfonyl fluoride),
   j. effect of surfactants: when stored in heavy duty liquid detergent of pH 11 at 40° C. for one week, 50% of the activity remains,
   k. molecular weight: 40,000 (gel filtration method using Toyopearl HW-55), and
   l. isoelectric point: 5.1 (isoelectric focusing electrophoresis method using Pharmaltye 3-10).

3. An alkaline protease-producing microorganism belonging to the genus Bacillus selected from the group consisting of Bacillus sp. Y (FERM BP-1029), Bacillus sp. P (FERM BP-1030), Bacillus sp. K (FERM BP-1031) and Bacillus sp. X (FERM) BP-1032) and having the following microbiological properties:
   A. morphological properties:
   the following morphological properties being observed when cultured on nutrient agar medium at 35° for 2 days;
      a. shape and size of cell: rods, measuring 0.4–0.5 $\mu m \times 1.6$–2.0 $\mu m$,
      b. Pleomorphism: no pleomorphism
      c. Motility: having peritrichous flagella and showing mobility,
      d. spore: producing endo spores; cells distending around the termini in the course of formation; matured spores being of a lemon shape, measuring 0.7–1.0 $\mu m \times 1.0$–1.8 $\mu m$,
      e. Gram stain: positive,
      f. acid-fastness: negative,
   B. cultural properties
      a. nutrient agar plate culture: growing at pH 7.0 to form round, flat or umbilicate, entire or undulate colonies, the surface of the colonies being smooth and glossy; growing at pH 10.0 to form round, flat and entire colonies, the surface of the colonies being smooth and glossy,
      b. nutrient agar slant culture: growing at pH 7.0 and pH 10.0 in the form of a strip or a broad strip to form glossy and cream-colored or pale brown colonies,
      c. nutrient liquid culture: growing at pH 7.0 to form no pellicle; growing at pH 10.0 to form no bacterial pellicle,
      d. gelatin stab culture: slightly liquefied at pH 7.0; liquefied at pH 10.0,
      e. litmus milk: growing poorly at pH 7.0; growing at pH 10.0, no coagulation of milk being observed, and change in color of litmus being unknown because of alkalinity of the medium,
   C. pysiological properties a. reduction of nitrate: positive,
b. denitrification: negative,
c. MR test: negative,
d. VP test: negative,
e. production of indole: negative,
f. production of hydrogen sulfide: negative,
g. hydrolysis of starch: positive,
h. utilization of citric acid: not utilizing in Koser's medium, but slightly utilizing in Christensen's medium,
i. utilization of inorganic nitrogen sources: not utilizing nitrates; not utilizing ammonium salts,
j. production of pigment: no pigment formed,
k. urease: positive,
l. oxidase: positive,
m. catalase: positive,
n. temperature range for growth: around 20° to 47° C., particularly around 33° to 35° C.,
o. pH range for growth: around 6.0 to 12.0, particularly 10,
p. behavior to oxygen: aerobic,
q. O-F test: negative,
r. production of acids and gases from saccharides: (+, produced; —, not produced)

| Saccharides | acid | gas |
| --- | --- | --- |
| L-arabinose | — | — |
| D-xylose | — | — |
| D-glucose | + | — |
| D-mannose | + | — |
| D-fructose | + | — |
| D-galactose | — | — |
| maltose | + | — |
| sucrose | + | — |
| lactose | — | — |
| trehalose | + | — |
| D-sorbitol | — | — |
| D-mannitol | + | — |
| inositol | — | — |
| glycerol | — | — |
| starch | + | — |

D. other properties
  a. resistance to sodium chloride: growing in 10% NaCl,
  b. producing alkaline proteases which have an optimal pH of 10 or higher and excellent stability in highly alkaline conditions in the presence of detergent constituents and which contribute to improving detergency.

4. The microorganism as described in claim 3, wherein said microorganism is Bacillus sp Y (FERM BP-1029).

5. The microorganism as described in claim 3, wherein said microorganism is Bacillus sp P (FERM BP-1030).

6. The microorganism as described in claim 3, wherein said microorganism is Bacillus sp K (FERM BP-1031).

7. The microorganism as described in claim 3, wherein said microorganism is Bacillus sp X (FERM BP-1032).

8. The microorganism as described in claim 3, wherein the alkaline protease is alkaline protease Ya.

9. The microorganism as described in claim 3, wherein the alkaline protease is alkaline protease Yb.

10. A process for the production of alkaline protease Ya as defined in claim 1, said process comprising cultivating alkaline protease-producing bacterium Bacillus sp. Y (FERM BP-1029), and isolating and recovering alkaline protease Ya from the culture.

11. A process for the production of alkaline protease Yb defined in claim 2, said process comprising cultivating alkaline protease-producing bacterium Bacillus sp. Y (FERM-1029), and isolating and recovering alkaline protease Yb from the culture.

* * * * *